(12) United States Patent
Peters et al.

(10) Patent No.: US 12,053,652 B2
(45) Date of Patent: Aug. 6, 2024

(54) WEARABLE AND AUTOMATED ULTRASOUND THERAPY DEVICES AND METHODS

(71) Applicant: CSW Therapeutics AB, Stockholm (SE)

(72) Inventors: Filip Ludwig Peters, Domsten (SE); Christopher Lee Stokely, Houston, TX (US); Mena Nadum, Gothenburg (SE)

(73) Assignee: CSW Therapeutics AB, Stockholm (SE)

(*) Notice: Subject to any disclaimer, the term of this patent is extended or adjusted under 35 U.S.C. 154(b) by 0 days.

(21) Appl. No.: 18/155,063

(22) Filed: Jan. 16, 2023

(65) Prior Publication Data
US 2023/0149746 A1    May 18, 2023

Related U.S. Application Data

(63) Continuation-in-part of application No. PCT/EP2022/069521, filed on Jul. 12, 2022.
(Continued)

(30) Foreign Application Priority Data

Jul. 12, 2021  (EP) .................................. 21185026

(51) Int. Cl.
*A61N 7/00*   (2006.01)

(52) U.S. Cl.
CPC ........ *A61N 7/00* (2013.01); *A61N 2007/0078* (2013.01)

(58) Field of Classification Search
CPC .................... A61N 7/00; A61N 2007/0078
See application file for complete search history.

(56) References Cited

U.S. PATENT DOCUMENTS

2002/0032394 A1* 3/2002 Brisken .............. A61B 17/2202
                                                        601/2
2003/0036706 A1* 2/2003 Slayton ................ A61B 8/5223
                                                        600/439
(Continued)

FOREIGN PATENT DOCUMENTS

JP          2020512846 A       4/2020
KR          102111453 B1       5/2020
WO       WO 2019225840       11/2019

OTHER PUBLICATIONS

Natalya Mizrahi et al., Ultrasound-Induced Angiogenic Response in Endothelial Cells, Ultrasound in Med. & Biol., pp. 1818-1829, 2007, vol. 33, No. 11, World Federation for Ultrasound in Medicine & Biology, USA.
(Continued)

*Primary Examiner* — Hien N Nguyen
(74) *Attorney, Agent, or Firm* — Silver Legal LLC; Jarrett L. Silver

(57) ABSTRACT

An ultrasound therapy device for generating ultrasound therapy. The ultrasound therapy device includes a wearable structure, ultrasound transducer units, a tightening mechanism, a memory, and a processor. The wearable structure is securable to a user to transmit the ultrasound to a target therapy area of a user including at least one of a kidney region, a lung region, and a lower limb of the user. The ultrasound transducer units are attachable and repositionable in the wearable structure to generate and deliver the ultrasound to the target region. The ultrasound transducer units are arranged in an array. The array of ultrasound transducer units is mechanically moved within the wearable structure and is in contact with a material to facilitate penetration of ultrasound into the user's body.

27 Claims, 12 Drawing Sheets

Related U.S. Application Data

(60) Provisional application No. 63/479,544, filed on Jan. 11, 2023, provisional application No. 63/480,000, filed on Jan. 14, 2023.

(56) References Cited

U.S. PATENT DOCUMENTS

| | | | |
|---|---|---|---|
| 2003/0139674 A1* | 7/2003 | Stergiopoulos | A61B 7/045 600/490 |
| 2005/0165298 A1* | 7/2005 | Larson | A61N 7/02 600/410 |
| 2006/0100530 A1* | 5/2006 | Kliot | A61B 5/681 600/483 |
| 2006/0241522 A1* | 10/2006 | Chandraratna | A61N 7/00 601/2 |
| 2011/0087115 A1 | 4/2011 | Sackner et al. | |
| 2016/0051149 A1* | 2/2016 | Viator | A61B 5/445 600/407 |
| 2016/0136462 A1 | 5/2016 | Lewis, Jr. et al. | |
| 2017/0136265 A1* | 5/2017 | Hyde | A61N 7/00 |
| 2017/0196761 A1* | 7/2017 | Hyde | A61M 16/0069 |
| 2019/0117243 A1 | 4/2019 | Khokhlova et al. | |
| 2021/0370064 A1* | 12/2021 | Murphy | A61B 5/4836 |

OTHER PUBLICATIONS

James Collis et al., Cavitation microstreaming and stress fields created by microbubbles, Ultrasonics, pp. 273-279, 50, Elsevier B.V, 2010.

Julien Milles; International Search Report and Written Opinion in European Patent Office in PCT/EP2022/069521, Oct. 14, 2022.

\* cited by examiner

WEARABLE AND AUTOMATED ULTRASOUND THERAPY DEVICES AND METHODS

PRIORITY

This application is a continuation-in-part of, claims priority to and the benefit of PCT/EP2022/069521 filed on Jul. 12, 2022, which claims benefit of and priority to European Patent Application No. EP21185026.8 filed on Jul. 12, 2021. This application also claims priority to and benefit of U.S. Provisional Patent Application Nos. 63/479,544 and 63/480,000 filed respectively on Jan. 11, 2023 and on Jan. 14, 2023.

INCORPORATION BY REFERENCE

This application incorporates by reference U.S. Provisional Patent Application No. 63/479,544 filed on Jan. 11, 2023, U.S. Provisional Patent Application No. 63/480,000 filed on Jan. 14, 2023, PCT Application No. PCT/EP2022/069521 filed on Jul. 12, 2022, and EP Application No. EP2118506.8 filed Jul. 12, 2021 in their entirety. In the event of any conflicts between those applications and this application, the construction of terms in this application will govern.

BACKGROUND

Technical Field

The specification is generally directed toward wearable and/or automated ultrasound therapy devices. More particularly, but not limited to, a wearable and automated ultrasound therapy device for treating kidney disease, inducing pulmonary rehabilitative effects, treating peripheral artery disease, and treating deep vein thrombosis.

Description of the Related Art

Typically, the human body's kidneys function to filter out extra fluid and certain ions. Renovascular disease patients have substantially impaired kidney function due to one or more of chronic renal disease (CRD), diabetic kidney disease and acute kidney injury may be characterized by a gradual decline in renal function over months or years. Angio-genetic, anti-inflammatory and/or regenerative therapy can be important goals of treatment in these diseases.

Further, pulmonary rehabilitation (PR) enables people with lung problems to breathe and live more comfortably. With lung conditions like chronic obstructive pulmonary disease (COPD) or Idiopathic Pulmonary Fibrosis (Ipf), a patient could need pulmonary rehabilitation with the goal of inducing anti-inflammatory and/or muscle relaxing effects or inducing angiogenesis and blood circulation to aid the body in breaking down fibrous tissue.

Further, deep vein thrombosis (DVT) occurs when a blood clot (thrombus) forms in one or more of the deep veins in the body, usually in the legs which can cause leg pain or swelling. Reducing swelling and inducing anti-thrombotic effects is an important goal of therapy.

Furthermore, a common disorder called peripheral arterial disease causes arteries to constrict, reducing blood flow to the arms or legs. In peripheral artery disease (PAD), the blood supply to the legs or arms or the legs is insufficient to meet demand. Other symptoms, such as claudication, may result from this. Typically, peripheral artery disease indicates an accumulation of fatty deposits in the arteries (atherosclerosis). Vascular narrowing brought on by atherosclerosis can lessen blood flow to the arms and legs. Revascularization can be an appropriate therapeutic goal for PAD.

Low intensity ultrasound treatment methods have been used in treating soft tissue injuries or damage and reducing fatty deposits commonly known as cellulite.

Some devices generate low-intensity ultrasound. U.S. Pat. No. 10,058,340B2 issued to Iulian Cioanta et al. discloses an ultrasound applicator that includes housing multiple reflectors with ultrasound generators projecting into a shared cavity. The multiple ultrasound generators can produce a variety of ultrasound focal volumes and wavefronts for medical treatment. Further, US patent application US20200206072A1 published by Christopher Capelli et al. discloses a method for acoustic treatment of tissue to disperse vacuoles within the tissue. The method includes a step of directing pulsed acoustic waves from the acoustic wave generator into the tissue containing the vacuoles. Further, the method of Christopher Capelli et al. includes a step of identifying the location of tissue containing vacuoles, and/or coupling (e.g., acoustically) an acoustic wave generator to the tissue containing the vacuoles.

SUMMARY

The above devices are intended to be utilized by a trained, and skilled medical professional who can apply the treatment to a patient in a clinical setting. Furthermore, the existing devices are costly and require specific knowledge about human anatomy, treatment protocol, regimen, pressure to be applied by the device, duration, and frequency of treatment. Further, these devices cannot track the health status of the user over time.

To the Applicant's knowledge, no wearable ultrasound therapy devices exist that utilize ultrasound for automatically treating kidney disease, inducing pulmonary rehabilitative effects, treating peripheral artery disease, and/or treating deep vein thrombosis.

This specification recognizes that there is a need for a portable, cost-effective, and efficient wearable and automated ultrasound therapy device to improve and measure pulmonary function, renal function, peripheral arterial function, and deep vein thrombosis (DVT) symptoms. Further, there is a need for a device that does not require a medical professional and/or assistant to have any specific abilities or training for ultrasound-based treatment of kidney disease, inducing pulmonary rehabilitative effects, peripheral artery disease, and deep vein thrombosis. Furthermore, there is a need for a wearable and automated ultrasound therapy device that can reduce the requirement for hospital-based visits and reduce the amount of resources needed by the hospital to treat a patient.

The approaches described in this section are approaches that could be pursued, but these are not necessarily approaches that have been previously conceived or pursued. Therefore, unless otherwise indicated, it should not be assumed that any of the approaches described in this section qualify as prior art merely by virtue of their inclusion in this section.

A wearable and automated ultrasound therapy device for treating kidney disease, inducing pulmonary rehabilitative effects, treating peripheral artery disease, and treating deep vein thrombosis is provided, as shown in and/or described in connection with at least one of the figures.

One aspect of the present disclosure relates to an ultrasound therapy device for generating ultrasound therapy. The ultrasound therapy device includes a wearable structure, a grouping of ultrasound transducer units, a tightening mechanism, a memory, and a processor. The wearable structure is securable to a user to transmit the ultrasound to a target therapy area of a user including at least one of a kidney region, a lung region, and a lower limb of the user. The ultrasound transducer units are attachable and repositionable in the wearable structure to generate and deliver the ultrasound to the target region. The ultrasound transducer units are arranged in an array. The array of ultrasound transducer units is mechanically moved within the wearable structure and is in contact with a material to facilitate penetration of ultrasound into the user's body. Adequate adhesion to the user's skin to facilitate ultrasound tissue penetration is assessed prior to ultrasound transmission. The tightening mechanism adjusts tightness. The ultrasound therapy device is connected to at least one minimally invasive physiological sensor to collect a health status data of the user. A memory includes ultrasound therapy instructions. A processor processes the ultrasound therapy instructions. The ultrasound therapy instructions comprising: determining a non-acute health status of the user based on health status data of the user received by the ultrasound therapy device or a computing device from a minimally invasive physiological sensor; receiving ultrasonic data from the ultrasound transducer units; determining a location of the array of ultrasound transducer units on the user's body; transmitting ultrasound therapy information to the one or more ultrasound transducer units; and generating ultrasound therapy in a target therapy area of the user, after a non-acute health state of the user and correct location of the array has been established.

In an embodiment, the minimally invasive physiological sensor is selected from a group consisting of one or more minimally invasive sensors including but not limited to an electrocardiography (ECG) sensor, photoplethysmography (PPG) sensor, seismocardiography (SCG) sensor, ballistocardiography (BCG) sensor, phonocardiography (PCG) sensor, ultrasonic sensor, temperature sensor, blood pressure sensor, bioimpedance sensor, electromyography (EMG), blood biomarker, pacemaker, glucose sensor, cochlear implants, implantable defibrillators, electroencephalogram (EEG), pulse oximeters, deep brain stimulators, retina implants, intracardiac pressure monitoring sensors and/or a piezoelectric sensor. Minimally invasive sensors as used herein include non-invasive sensors.

In an embodiment, the ultrasound therapy information includes at least one of frequency, temporal average, duty cycle, and therapy duration.

In an embodiment, the ultrasound therapy device includes a minimally invasive sensor for minimally invasively acquiring one or more of: pulmonary function information, renal function information, peripheral arterial function, and deep vein thrombosis (DVT) function information of the user.

In an embodiment, an acoustic sensor is facing away from the user's skin to enable the detection of environmental acoustic disturbances that could interfere with receiving and sending signals.

In an embodiment, the pulmonary function information comprises one or more minimally invasive data from the lungs and self-reported pulmonary health data.

In an embodiment, the renal function information comprises one or more minimally invasive data from the kidney and self-reported kidney health data.

In an embodiment, the deep vein thrombosis (DVT) function information comprises one or more minimally invasive data from the lower limb and self-reported lower limb health data.

In an embodiment, the peripheral arterial function information comprises one or more minimally invasive data from the lower limb and self-reported lower limb health data In an embodiment, the processor is configured to receive pulmonary function information, and transmit ultrasound therapy information to the one or more ultrasound transducer units for generating ultrasound therapy.

In an embodiment, the processor is configured to receive renal function information, and transmit ultrasound therapy information to the one or more ultrasound transducer units for generating ultrasound therapy.

In an embodiment, the processor is configured to receive deep vein thrombosis (DVT) function information and transmit ultrasound therapy information to the one or more ultrasound transducer units for generating ultrasound therapy.

In an embodiment, the processor is configured to receive peripheral arterial function information and transmit ultrasound therapy information to the one or more ultrasound transducer units for generating ultrasound therapy.

In an embodiment, the ultrasound therapy information is configured to induce pulmonary rehabilitative effects.

In an embodiment, the ultrasound therapy information is configured to promote one or more of angiogenesis, reduce inflammation, reduce fibrosis and tubular injury, increase neovascularization, and ameliorate inflammatory processes.

In an embodiment, the ultrasound therapy information is configured to diminish sodium reabsorption at different sites in the nephron, thereby increasing urinary sodium and water losses, and inhibit water reabsorption by blocking vasopressin receptors along the connecting tubule and collecting duct with the goal of inducing negative body fluid balance.

In an embodiment, the ultrasound therapy is administered in one or more patients diagnosed with one or more of bronchitis, Chronic Obstructive Pulmonary Disease, Cystic Fibrosis, Emphysema, Idiopathic Pulmonary Fibrosis, flu, lung cancer, obstructive sleep apnea, pleurisy, Tuberculosis, pulmonary congestion, congestive organ failure, kidney diseases, and peripheral artery disease.

In an embodiment, the ultrasound therapy device includes a circuit board to connect the one or more ultrasound transducer units, the minimally invasive sensor(s), the positioning mechanism, and the processor.

In an embodiment, the ultrasound therapy device comprises a proximity sensor.

In an embodiment, the proximity sensor is a pressure sensor for measuring the pressure that the one or more ultrasound transducer units apply on the user's skin.

In an embodiment, the ultrasound therapy device includes an inertial measurement unit (IMU) sensor 115 configured to determine whether the ultrasound therapy device is correctly positioned on the user's skin and/or determines user movement.

In an embodiment, the ultrasound therapy device includes a housing for accommodating at least a part of one or more ultrasound transducer units, the proximity sensor, and the processor.

In an embodiment, the processor is configured to analyze one or more of the pulmonary function information, the renal function information, and/or the deep vein thrombosis (DVT) function of one or more of the lung, the kidney, and the lower limb of the user and determine one or more locations on the lung, the kidney and the lower limb of the user where the one or more of the ultrasound signals are focused based on ultrasonic sensor data of the one or more ultrasound transducer units.

In an embodiment, the circuit board is a PCB connected to one or more of: an analog-to-digital converter (ADC) for converting analog ultrasonic data into digital data; a microcontrolling unit with a power and data transmission port; one or more large bandwidth operational amplifiers circuits; a plurality of digital buffers; at least two signal mixers for precise doppler calculation; a plurality of filters suitable for an operating range of a piezoelectric ultrasonic sensor; a plurality of bidirectional drivers for a micro linear actuator and a servo motor; and a plurality of headers and a plurality of PWM lines to provide the power to the micro linear actuator and the servo motor.

In an embodiment, the ultrasound therapy device includes a boost circuit for providing power feed to the one or more ultrasound transducer units.

In an embodiment, the boost circuit comprises a low equivalent series resistance (ESR) capacitor and utilizes an accumulated charge on high capacitance.

In an embodiment, the ultrasound therapy information comprises location data, frequency data, spatial average temporal average data, duty cycle data, and therapy duration data.

In an embodiment, the array is configured to direct the ultrasound beam to the one or more regions of the lung the kidney, and the lower limb and execute the ultrasound therapy information in the one or more regions.

In an embodiment, the ultrasound therapy device is configured to compare the pulmonary, renal, deep vein thrombosis or peripheral arterial health of the user in the one or more regions over time to determine the efficacy of the ultrasound therapy.

In an embodiment, the ultrasound therapy device is configured to update the ultrasound therapy based on the observed efficacy and safety of the ultrasound therapy over time.

In an embodiment, the ultrasound therapy device is configured to create a map of the user's lungs, kidneys, and lower limbs.

In an embodiment, the ultrasound therapy device is configured to collect information on the user's health condition through a questionnaire and/or patient health database.

In an embodiment, the ultrasound therapy device includes a pressure adjustment mechanism configured to adjust the tightness of the ultrasound transducer units to the user's skin.

In an embodiment, the ultrasound therapy device receives power through a cable from an external electric power system.

In an embodiment, the ultrasound therapy device includes an impedance matching material, gel, or fluid in the form of removable ultrasound gel that is connected to the skin-facing side of the ultrasound therapy device.

Accordingly, one advantage of the present invention is that it provides a portable, cost-effective, and efficient wearable and automated ultrasound therapy device to obtain and measure pulmonary function, renal function, peripheral arterial function, and deep vein thrombosis (DVT) function by generating ultrasound therapy.

Accordingly, one advantage of the present invention is that it does not require a medical professional and/or assistant to have any specific abilities or training for treating kidney disease, inducing pulmonary rehabilitative effects, peripheral artery disease, and deep vein thrombosis.

Accordingly, one advantage of the present invention is that it provides a wearable and automated ultrasound therapy device that can reduce the requirement for hospital-based visits and reduce the number of resources needed by the hospital to treat a patient.

Accordingly, one advantage of the present invention is that it automates the continuous positioning of the ultrasound transducer unit and the acquisition of sensor data.

Accordingly, one advantage of the present invention is that the continuous positioning of the ultrasound transducer unit is automated with an artificial intelligence-based system approach such as a Case-Based Expert System, and/or a fuzzy logic control system.

Accordingly, one advantage of the present invention is that it provides a personalized ultrasound therapy parameter that can be calculated by a machine learning model. Consequently, the ultrasound therapy device can be configured to continuously identify, and scan regions of the kidneys, lungs, and lower limbs of the user that need to be treated and apply region-based ultrasounds.

Other embodiments and advantages will become readily apparent to those skilled in the art upon viewing the drawings and reading the detailed description hereafter, all without departing from the spirit and the scope of the disclosure. The drawings and detailed descriptions presented are to be regarded as illustrative in nature and not in any way as restrictive.

The present disclosure further relates to a device configured to provide a semi-automated ultrasound treatment. Firstly, the user can receive ultrasound therapy information such as disease type that needs to be treated and therapy region, e.g. ischemia and/or organ muscle stiffness. The user can position the device to the therapy region using previously mapped out organ regions from a first-time use calibration process. Then the device can provide the ultrasonic data and/or electronic stethoscope data (and/or other minimally invasive physiological parameter data of the user) from the therapy region to the user. The user can therefore analyze severity of the disease. The risk analysis may be assessed by a risk assessment machine learning model and/or measurement of health function of the user. Then the user can identify the ultrasound therapy parameters such as intensity, duration, and/or pulsation frequency in one or more regions based on the user's characteristics such as body size, age, type, and/or severity of organ disease (e.g. organ muscle stiffness may require an ultrasound therapy to relax the muscle and ischemia may require an ultrasound therapy for regenerative therapy). Lastly, the user can administer the ultrasound therapy based on the identified therapy needs.

In some aspects, the techniques described herein relate to an ultrasound therapy device for generating ultrasound therapy, the ultrasound therapy device including: a housing including a skin-facing side; a grouping of ultrasound transducer units on the skin-facing side to generate and deliver ultrasound to a target therapy area of a user including at least one of a kidney region, a lung region, and a lower limb of the user, the grouping of ultrasound transducer units configured to operate directly through skin of the user near the target therapy area or indirectly through an impedance matching material, gel or fluid near the target therapy area; a communications bus to receive from a minimally invasive physiological sensor a health status data of the user; memory including ultrasound therapy instructions; and a processor for processing the ultrasound therapy instructions, the ultrasound therapy instructions including: determining a non-acute health status of the user based on the health status data of the user received from the minimally invasive physiological sensor; receiving ultrasonic data from the ultrasound transducer units; determining a body location of the grouping of ultrasound transducer units from the ultrasonic data; transmitting ultrasound therapy information to the ultrasound transducer units; and generating ultrasound therapy by the ultrasound transducer units in a target therapy area of the user, after a non-acute health state of the user and the body location of the grouping has been established and determined to be acceptable.

In some aspects, the techniques described herein relate to an ultrasound therapy device, wherein at least some of the ultrasound transducer units of the grouping can be partially or fully utilized to allow for beam steering of the ultrasound and shifting focal points of the ultrasound to a desired location of the target therapy area.

In some aspects, the techniques described herein relate to an ultrasound therapy device, further including: a pressure sensor to measure proximity of the ultrasound transducer units to the skin of the user to determine adequate skin-transducer contact, wherein the determining the body location of the grouping of ultrasound transducer units is further based on readings from the pressure sensor.

In some aspects, the techniques described herein relate to an ultrasound therapy device, the processor generates an ultrasound using phased arrays of the ultrasound transducer units by adjusting a phase and a magnitude of each ultrasound transducer.

In some aspects, the techniques described herein relate to an ultrasound therapy device, wherein the grouping of ultrasound transducers is arranged in an array.

In some aspects, the techniques described herein relate to an ultrasound therapy device, wherein the impedance matching material, gel or fluid is ultrasound gel or an ultrasound gel patch.

In some aspects, the techniques described herein relate to an ultrasound therapy device, wherein the minimally invasive physiological sensor is selected from the group consisting of minimally invasive sensors 134.

In some aspects, the techniques described herein relate to an ultrasound therapy device, wherein the ultrasound therapy information includes at least one of frequency, temporal average, duty cycle, and therapy duration.

In some aspects, the techniques described herein relate to an ultrasound therapy device, further including: a wearable structure securable to the user, wherein the housing is attachable and repositionable in the wearable structure to target the target therapy area.

In some aspects, the techniques described herein relate to an ultrasound therapy device, further including: a tightening mechanism to adjust tightness of the wearable structure around the body of the user and secure the ultrasound therapy device in position to target the target therapy area and prevent unwanted dispersion of the ultrasound.

In some aspects, the techniques described herein relate to an ultrasound therapy device, further including: sending and receiving ultrasonic waves from the ultrasound transducers to test expected throughput of the impedance matching material, gel or fluid and skin contact; determine if expected throughput is allowable based on a pre-existing threshold; and instruct the processor to start ultrasound therapy if expected throughput is allowable.

In some aspects, the techniques described herein relate to an ultrasound therapy device, wherein the housing is part of a handheld computing device or attachment of the handheld computing device, and the user can interact with a touch-screen display in communication with the ultrasound therapy device on the handheld computing device.

In some aspects, the techniques described herein relate to an ultrasound therapy device, wherein the handheld computing device is a smartphone.

In some aspects, the techniques described herein relate to an ultrasound therapy device, including a minimally invasive sensor 134 for minimally invasively acquiring one or more of: pulmonary function information, renal function information, peripheral arterial function, deep vein thrombosis (DVT) function information of the user.

In some aspects, the techniques described herein relate to an ultrasound therapy device, wherein a second acoustic sensor is facing away from the skin-facing side and the processor is configured to enable detection and removal of surrounding acoustic disturbances sensed by the second acoustic sensor that could interfere with receiving and sending signals.

In some aspects, the techniques described herein relate to an ultrasound therapy device, wherein the pulmonary function information includes one or more minimally invasive, imaging and/or biomarker data from the lungs and self-reported pulmonary health data.

In some aspects, the techniques described herein relate to an ultrasound therapy device, wherein the renal function information includes one or more minimally invasive, imaging and/or biomarker data from the kidney and self-reported kidney health data.

In some aspects, the techniques described herein relate to an ultrasound therapy device, wherein the deep vein thrombosis (DVT) function information includes one or more minimally invasive, imaging and/or biomarker data from the lower limb and self-reported lower limb health data.

In some aspects, the techniques described herein relate to an ultrasound therapy device, wherein the processor is configured to receive pulmonary function information and transmit ultrasound therapy information to the one or more ultrasound transducer units for generating ultrasound therapy.

In some aspects, the techniques described herein relate to an ultrasound therapy device, wherein the processor is configured to receive renal function information and transmit ultrasound therapy information to the one or more ultrasound transducer units for generating ultrasound therapy.

In some aspects, the techniques described herein relate to an ultrasound therapy device, wherein the processor is configured to receive deep vein thrombosis (DVT) function information, and transmit ultrasound therapy information to the one or more ultrasound transducer units for generating ultrasound therapy.

In some aspects, the techniques described herein relate to an ultrasound therapy device, wherein the ultrasound therapy information is configured to induce pulmonary rehabilitative effects.

In some aspects, the techniques described herein relate to an ultrasound therapy device, wherein the processor carries out instructions to promote one or more of angiogenesis, reduce inflammation, improve renal fibrosis and tubular injury, neovascularization, and ameliorating inflammatory processes.

In some aspects, the techniques described herein relate to an ultrasound therapy device, wherein the ultrasound therapy is configured to treat one or more of bronchitis, Chronic Obstructive Pulmonary Disease, Cystic Fibrosis, Emphysema, Idiopathic Pulmonary Fibrosis, flu, lung cancer, obstructive sleep apnea, pleurisy, Tuberculosis, pulmonary congestion, kidney diseases, and peripheral artery disease.

In some aspects, the techniques described herein relate to an ultrasound therapy device, further including: a circuit board in communication at least one of the ultrasound transducer units, a pressure sensor, an acoustic sensor, a positioning mechanism, and the processor.

In some aspects, the techniques described herein relate to an ultrasound therapy device, wherein a pressure sensor is configured to measure pressure that the ultrasound transducer units apply on the skin.

In some aspects, the techniques described herein relate to an ultrasound therapy device, further includes an inertial measurement unit (IMU) sensor configured to determine at least one 1, wherein the housing accommodates at least a part of each of the ultrasound transducer units, a pressure sensor, and the processor.

In some aspects, the techniques described herein relate to an ultrasound therapy device, wherein the processor is configured to analyze one or more of the pulmonary function information, the renal function information, and/or the deep vein thrombosis (DVT) function of one or more of the lung, the kidney, and the lower limb of the user and determine one or more locations on the lung, the kidney, and the lower limb of the user where the one or more of the ultrasound are focused based on ultrasonic sensor data of one or more ultrasound transducer units.

In some aspects, the techniques described herein relate to an ultrasound therapy device, wherein the circuit board is a PCB connected to one or more of: an analog-to-digital converter (ADC) for converting analog ultrasonic data into digital data; a micro-controlling unit with a power and data transmission port; large bandwidth operational amplifiers circuit; a plurality of digital buffers; at least two signal mixers for precise doppler calculation; a plurality of filters suitable for an operating range of a piezoelectric ultrasonic sensor; a pulse width modulation control; a plurality of bidirectional drivers for a micro linear actuator and a servo motor; and a plurality of headers and a plurality of PWM lines to provide the power to the micro linear actuator and the servo motor.

In some aspects, the techniques described herein relate to an ultrasound therapy device, including a boost circuit for providing power feed to the one or more of the ultrasound transducer units.

In some aspects, the techniques described herein relate to an ultrasound therapy device, wherein the boost circuit includes a low equivalent series resistance (ESR) capacitor and utilizes an accumulated charge on high capacitance.

In some aspects, the techniques described herein relate to an ultrasound therapy device, wherein the ultrasound therapy information includes location data, frequency data, spatial average temporal average data, duty cycle data, and therapy duration data.

In some aspects, the techniques described herein relate to an ultrasound therapy device, the ultrasound therapy is configured to compare pulmonary or renal health of the user in one or more regions over time to determine efficacy of the ultrasound therapy.

In some aspects, the techniques described herein relate to an ultrasound therapy device, the processor is configured to update the ultrasound therapy based on the determined efficacy of the ultrasound therapy over time.

In some aspects, the techniques described herein relate to an ultrasound therapy device, the processor is configured to create a map of the user's lung, kidney, and the lower limb from signal received by the ultrasound transducers or other sensors.

In some aspects, the techniques described herein relate to an ultrasound therapy device, the processor is configured to collect information on a health condition of the user through at least one of a questionnaire and a patient health database.

In some aspects, the techniques described herein relate to an ultrasound therapy device, wherein the wearable structure includes a pressure adjustment mechanism configured to adjust proximity of the transducer units to the user's skin.

In some aspects, the techniques described herein relate to an ultrasound therapy device, wherein the ultrasound therapy device receives power through a cable from an external electric power system.

In some aspects, the techniques described herein relate to an ultrasound therapy device, the ultrasound therapy device further includes a removable ultrasound gel patch that is connected to the skin-facing side of the ultrasound therapy device.

In some aspects, the techniques described herein relate to a kit including the ultrasound therapy device, a wearable structure, and a removable ultrasound gel patch.

In some aspects, the techniques described herein relate to a kit including the ultrasound therapy device and ultrasound gel.

In some aspects, the techniques described herein relate to a kit including the ultrasound therapy device, a wearable structure, an impedance matching material, gel or fluid, and fixation pads.

In some aspects, the techniques described herein relate to a method of applying ultrasound therapy by a user, the method including steps of: providing the user with an ultrasound therapy device containing a housing with ultrasound transducers on a skin facing side of the housing, an impedance matching material, gel or fluid, and a user interface; applying by the user the impedance matching material, gel or fluid at or near a target therapy area including at least one of a kidney region, a lung region, and a lower limb of the user; holding by the user or fastening within a wearable structure the ultrasound therapy device against the impedance matching material, gel or fluid of the user at or near the target therapy area; sensing, by the ultrasound therapy device, and receiving, by the user interface, information regarding at least some of a location of the target therapy area, a location of the ultrasound therapy device relative to the target therapy area, a proximity of the ultrasound transducers to the skin of the user, a type of ultrasound therapy to perform, and a health status of the user; activating the ultrasound therapy by the user; and performing the ultrasound therapy on the user based on the information.

In some aspects, the techniques described herein relate to a method, further including: mapping out a sub skin layout of the target therapy area using the ultrasound transducers or other sensors on the device; and performing the ultrasound therapy on a portion of the layout.

In some aspects, the techniques described herein relate to a method, further including: focusing a laser from the ultrasound therapy device or another device below the user's skin near the target therapy area to create an ultrasound emanating from a focal point of the laser. Said ultrasound emanating from a focal point of the laser can be detected using ultrasound transducers and analyzed to determine a condition of said focal point.

In some aspects, the techniques described herein relate to a method, wherein the user interface on a smartphone or smart tablet receives instructions from the user.

In some aspects, the techniques described herein relate to a method, wherein the smartphone or smart tablet is integrated with or physically connected to the ultrasound therapy device.

In some aspects, the techniques described herein relate to an ultrasound system for generating ultrasound therapy, the ultrasound system including: an ultrasound therapy device, including; a housing including a skin-facing side; a grouping of ultrasound transducer units on the skin-facing side to generate and deliver ultrasound to a target therapy area of a user including at least one of a kidney region, a lung region, and a lower limb of the user, the grouping of ultrasound transducer units configured to operate directly through skin of the user near the target therapy area or indirectly through an impedance matching material, gel or fluid near the target therapy area; and a communications bus to receive from a minimally invasive physiological sensor a health status data of the user, and to exchange information and instructions from a processor and memory; the memory including ultrasound therapy instructions; and the processor for processing the ultrasound therapy instructions, the ultrasound therapy instructions including: determining a non-acute health status of the user based on the health status data of the user received from the minimally invasive physiological sensor; receiving ultrasonic data from the ultrasound transducer units; determining a body location of the grouping of ultrasound transducer units from the ultrasonic data; transmitting ultrasound therapy information to the ultrasound transducer units; and generating ultrasound therapy by the ultrasound transducer units in a target therapy area of the user, after a non-acute health state of the user and the body location of the grouping has been established and determined to be acceptable.

In some aspects, the techniques described herein relate to an ultrasound system for generating ultrasound therapy, the ultrasound system including: an ultrasound therapy device, including; a housing including a skin-facing side; a grouping of ultrasound transducer units on the skin-facing side to generate and deliver at a focal point of ultrasound waves ultrasound to a target therapy area of a user including at least one of a kidney region, a lung region, and a lower limb of the user, the grouping of ultrasound transducer units configured to operate directly through skin of the user near the target therapy area or indirectly through an impedance matching material, gel or fluid near the target therapy area; and a communications bus to receive from a minimally invasive physiological sensor a health status data of the user, and to exchange information and instructions from a processor and memory; the memory including ultrasound therapy instructions; and the processor for processing the ultrasound therapy instructions, the ultrasound therapy instructions including: determining a non-acute health status of the user based on the health status data of the user received from the minimally invasive physiological sensor; receiving ultrasonic data from the ultrasonic transducer units; determining a body location of the grouping of ultrasonic transducer units from the ultrasonic data; transmitting ultrasound therapy information to the ultrasonic transducer units; and generating ultrasound therapy at the focal point of ultrasound waves generated by the ultrasound transducer units in a target therapy area of the user, after a non-acute health state of the user and the body location of the grouping has been established and determined to be acceptable.

In some aspects, the techniques described herein relate to an ultrasound system, wherein at least some of the ultrasound transducer units of the grouping can be partially or fully utilized to allow for beam steering of the ultrasound and shifting focal points of the ultrasound to a desired location of the target therapy area.

In some aspects, the techniques described herein relate to an ultrasound system, further including: a pressure sensor to measure proximity of the ultrasound transducer units to the skin of the user to determine adequate skin-transducer contact, wherein the determining the body location of the grouping of ultrasound transducer units is further based on readings from the pressure sensor.

In some aspects, the techniques described herein relate to an ultrasound system, the processor generates an ultrasound using phased arrays of the ultrasound transducer units by adjusting a phase and a magnitude of each ultrasound transducer.

In some aspects, the techniques described herein relate to an ultrasound system, wherein the grouping of ultrasound transducers is arranged in an array.

In some aspects, the techniques described herein relate to an ultrasound system, wherein the array is arranged two- or three dimensionally.

In some aspects, the techniques described herein relate to an ultrasound system, wherein the impedance matching material, gel or fluid is ultrasound gel or an ultrasound gel patch.

In some aspects, the techniques described herein relate to an ultrasound system, wherein the minimally invasive physiological sensor is selected from the group consisting of minimally invasive sensors.

In some aspects, the techniques described herein relate to an ultrasound system, wherein the ultrasound therapy information includes at least one of frequency, temporal average, duty cycle, and therapy duration.

In some aspects, the techniques described herein relate to an ultrasound system, further including: a wearable structure securable to the user, wherein the housing is attachable and repositionable in the wearable structure to target the target therapy area.

In some aspects, the techniques described herein relate to an ultrasound system, further including: a tightening mechanism to adjust tightness of the wearable structure around the body of the user and secure the ultrasound therapy device in position to target the target therapy area and prevent unwanted dispersion of the ultrasound.

In some aspects, the techniques described herein relate to an ultrasound system, further including sending and receiving ultrasonic waves from the ultrasound transducers to test expected throughput of the impedance matching material, gel or fluid and skin contact; determine if expected throughput is allowable based on a pre-existing threshold; and instruct the processor to start ultrasound therapy if expected throughput is allowable.

In some aspects, the techniques described herein relate to an ultrasound system, wherein the housing is part of a handheld computing device or attachment of the handheld computing device, and the user can interact with a touchscreen display in communication with the ultrasound therapy device on the handheld computing device.

In some aspects, the techniques described herein relate to an ultrasound system, wherein the handheld computing device is a smartphone.

In some aspects, the techniques described herein relate to an ultrasound system, including an minimally invasive sensor for minimally invasively acquiring one or more of:

pulmonary function information, renal function information, peripheral arterial function, deep vein thrombosis (DVT) function information of the user.

In some aspects, the techniques described herein relate to an ultrasound system, wherein a second acoustic sensor is facing away from the skin-facing side and the processor is configured to enable detection and removal of surrounding acoustic disturbances sensed by the second acoustic sensor that could interfere with receiving and sending signals.

In some aspects, the techniques described herein relate to an ultrasound system, wherein the pulmonary function information includes one or more minimally invasive data from the lungs and self-reported pulmonary health data.

In some aspects, the techniques described herein relate to an ultrasound system, wherein the renal function information includes one or more minimally invasive data from the kidney and self-reported kidney health data.

In some aspects, the techniques described herein relate to an ultrasound system, wherein the deep vein thrombosis (DVT) function information includes one or more minimally invasive data from the lower limb and self-reported lower limb health data.

In some aspects, the techniques described herein relate to an ultrasound system, wherein the processor is configured to receive pulmonary function information and transmit ultrasound therapy information to the one or more ultrasound transducer units for generating ultrasound therapy.

In some aspects, the techniques described herein relate to an ultrasound system, wherein the processor is configured to receive renal function information and transmit ultrasound therapy information to the one or more ultrasound transducer units for generating ultrasound therapy.

In some aspects, the techniques described herein relate to an ultrasound system, wherein the processor is configured to receive deep vein thrombosis (DVT) function information, and transmit ultrasound therapy information to the one or more ultrasound transducer units for generating ultrasound therapy.

In some aspects, the techniques described herein relate to an ultrasound system, wherein the ultrasound therapy information is configured to induce pulmonary rehabilitative effects.

In some aspects, the techniques described herein relate to an ultrasound system, wherein the processor carries out instructions to promote one or more of angiogenesis, reduce inflammation, improve renal fibrosis and tubular injury, neovascularization, and ameliorating inflammatory processes.

In some aspects, the techniques described herein relate to an ultrasound system, wherein the ultrasound therapy is configured to treat one or more of bronchitis, Chronic Obstructive Pulmonary Disease, Cystic Fibrosis, Emphysema, Idiopathic Pulmonary Fibrosis, flu, lung cancer, obstructive sleep apnea, pleurisy, Tuberculosis, pulmonary congestion, kidney diseases, and peripheral artery disease.

In some aspects, the techniques described herein relate to an ultrasound system, further including: a circuit board in communication at least one of the ultrasound transducer units, a pressure sensor, an acoustic sensor, a positioning mechanism, and the processor.

In some aspects, the techniques described herein relate to an ultrasound system, wherein the pressure sensor is configured to measure pressure that the ultrasound transducer units applies on the skin.

In some aspects, the techniques described herein relate to an ultrasound system, further includes an inertial measurement unit (IMU) sensor configured to determine at least one of whether the ultrasound therapy device is correctly positioned on the skin and whether the user is moving.

In some aspects, the techniques described herein relate to an ultrasound system, wherein the housing accommodates at least a part of each of the ultrasound transducer units, a pressure sensor, and the processor.

In some aspects, the techniques described herein relate to an ultrasound system, wherein the processor is configured to analyze one or more of the pulmonary function information, the renal function information, and/or the deep vein thrombosis (DVT) function of one or more of the lung, the kidney, and the lower limb of the user and determine one or more locations on the lung, the kidney, and the lower limb of the user where the one or more of the ultrasound are focused based on ultrasonic sensor data of one or more ultrasound transducer units.

In some aspects, the techniques described herein relate to an ultrasound system, wherein the circuit board is a PCB connected to one or more of: an analog-to-digital converter (ADC) for converting analog ultrasonic data into digital data; a micro-controlling unit with a power and data transmission port; large bandwidth operational amplifiers circuit; a plurality of digital buffers; at least two signal mixers for precise doppler calculation; a plurality of filters suitable for an operating range of a piezoelectric ultrasonic sensor; a pulse width modulation control; a plurality of bidirectional drivers for a micro linear actuator and a servo motor; and a plurality of headers and a plurality of PWM lines to provide the power to the micro linear actuator and the servo motor.

In some aspects, the techniques described herein relate to an ultrasound system, including a boost circuit for providing power feed to the one or more of the ultrasound transducer units.

In some aspects, the techniques described herein relate to an ultrasound system, wherein the boost circuit includes a low equivalent series resistance (ESR) capacitor and utilizes an accumulated charge on high capacitance.

In some aspects, the techniques described herein relate to an ultrasound system, wherein the ultrasound therapy information includes location data, frequency data, spatial average temporal average data, duty cycle data, and therapy duration data.

In some aspects, the techniques described herein relate to an ultrasound system, the ultrasound therapy is configured to compare pulmonary or renal health of the user in one or more regions over time to determine efficacy of the ultrasound therapy.

In some aspects, the techniques described herein relate to an ultrasound system, the processor is configured to update the ultrasound therapy based on the determined efficacy of the ultrasound therapy over time.

In some aspects, the techniques described herein relate to an ultrasound system, the processor is configured to create a map of the user's lung, kidney, and the lower limb from signal received by the ultrasound transducers or other sensors.

In some aspects, the techniques described herein relate to an ultrasound system, the processor is configured to collect information on a health condition of the user through at least one of a questionnaire and a patient health database.

In some aspects, the techniques described herein relate to an ultrasound system, wherein the wearable structure includes a pressure adjustment mechanism configured to adjust proximity of the transducer units to the user's skin.

In some aspects, the techniques described herein relate to an ultrasound system, wherein the ultrasound therapy device receives power through a cable from an external electric power system.

In some aspects, the techniques described herein relate to an ultrasound system, the ultrasound therapy device further includes a removable ultrasound gel patch that is connected to the skin-facing side of the ultrasound system.

In some aspects, the techniques described herein relate to a kit including the ultrasound system, a wearable structure, and a removable ultrasound gel patch.

In some aspects, the techniques described herein relate to a kit including the ultrasound system and ultrasound gel.

In some aspects, the techniques described herein relate to a kit including the ultrasound system, a wearable structure, an impedance matching material, gel or fluid, and fixation pads.

Other features of the example embodiments will be apparent from the drawings and from the detailed description that follows.

BRIEF DESCRIPTION OF THE DRAWINGS

The accompanying drawings illustrate the embodiments of systems, methods, and other aspects of the disclosure. Any person of ordinary skill in the art will appreciate that the illustrated element boundaries (e.g., boxes, groups of boxes, or other shapes) in the figures represent an example of the boundaries. In some examples, one element may be designed as multiple elements, or multiple elements may be designed as one element. In some examples, an element shown as an internal component of one element may be implemented as an external component in another and vice versa. Furthermore, the elements may not be drawn to scale. Reference numerals may be selectively repeated across images for clarity or emphasis.

Various embodiments will hereinafter be described in accordance with the appended drawings, which are provided to illustrate, not limit, the scope, wherein similar designations denote similar elements, and in which.

DETAILED DESCRIPTION

The present description is best understood with reference to the detailed figures and description set forth herein. Various embodiments of the present system and method have been discussed with reference to the figures. However, those skilled in the art will readily appreciate that the detailed description provided herein with respect to the figures is merely for explanatory purposes, as the present system and method may extend beyond the described embodiments. For instance, the teachings presented and the needs of a particular application may yield multiple alternative and suitable approaches to implement the functionality of any detail of the present systems and methods described herein. Therefore, any approach to implement the present system and method may extend beyond certain implementation choices in the following embodiments.

According to an embodiment herein, the methods of the present invention may be implemented by performing or completing manually, automatically, and/or a combination of thereof. The term "method" refers to manners, means, techniques, and procedures for accomplishing any task including, but not limited to, those manners, means, techniques, and procedures either known to the person skilled in the art or readily developed from existing manners, means, techniques and procedures by practitioners of the art to which the present invention belongs. The persons skilled in the art will envision many other possible variations within the scope of the present system and method described herein.

One example of ultrasound are shockwaves. Generally, ultrasound is defined as either low intensity or high intensity by determining whether the energy is below or above 1 W/cm2. Further, the low-frequency and high-frequency ultrasound are classified by determining whether the frequency is below or above 1 MHz. The low frequency ultrasound has good penetration that can reach deeper targets and initiate predominantly mechanical effects on cell membranes with negligible temperature increase (<0.01° C.), thereby depolarizing membranes to activate voltage-gated sodium channels and voltage-gated calcium channels and to influence cells' excitability. However, high-frequency ultrasound has a shorter wavelength and better spatial resolution than low-frequency ultrasound. The high-frequency ultrasound is centrally deposited, which is helpful in imaging. Fast attenuation of the high-frequency ultrasound may cause thermal loss and poor penetration when applied to the delivery of skin treatment.

Ultrasound therapy includes methods such as unfocused beaming, hyperthermia, high intensity focused ultrasound (HIFU), focused ultrasound, extracorporeal lithotripsy, extracorporeal shockwave therapy, phacoemulsification, ultrasound assisted liposuction, tissue cutting and vessel sealing, skin permeabilization, low intensity pulsed ultrasound.

Figures 1A, 1B:
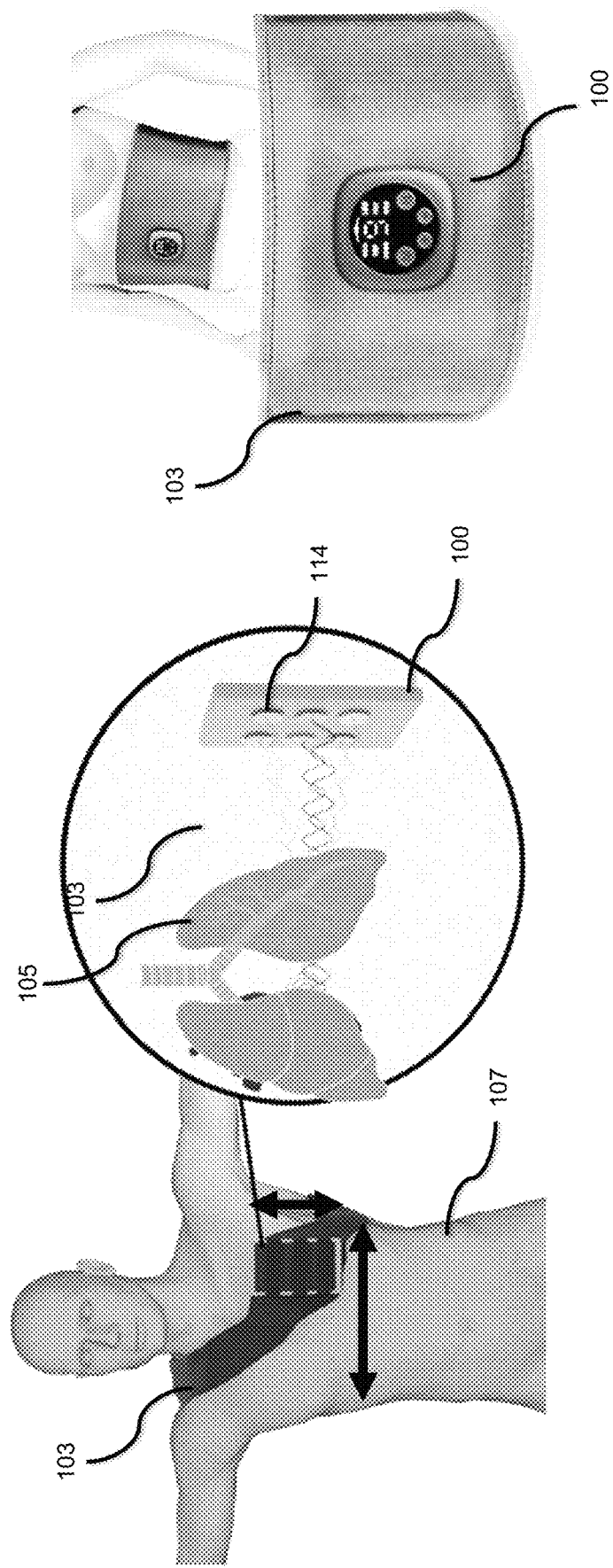
FIG. 1A illustrates a perspective view of an example wearable structure that allows the ultrasound therapy device to target the kidney region, or the lung region of the user.
FIG. 1B illustrates a perspective view of another example wearable structure that allows the ultrasound therapy device to target the diaphragm or stomach of the user
Figure 2:
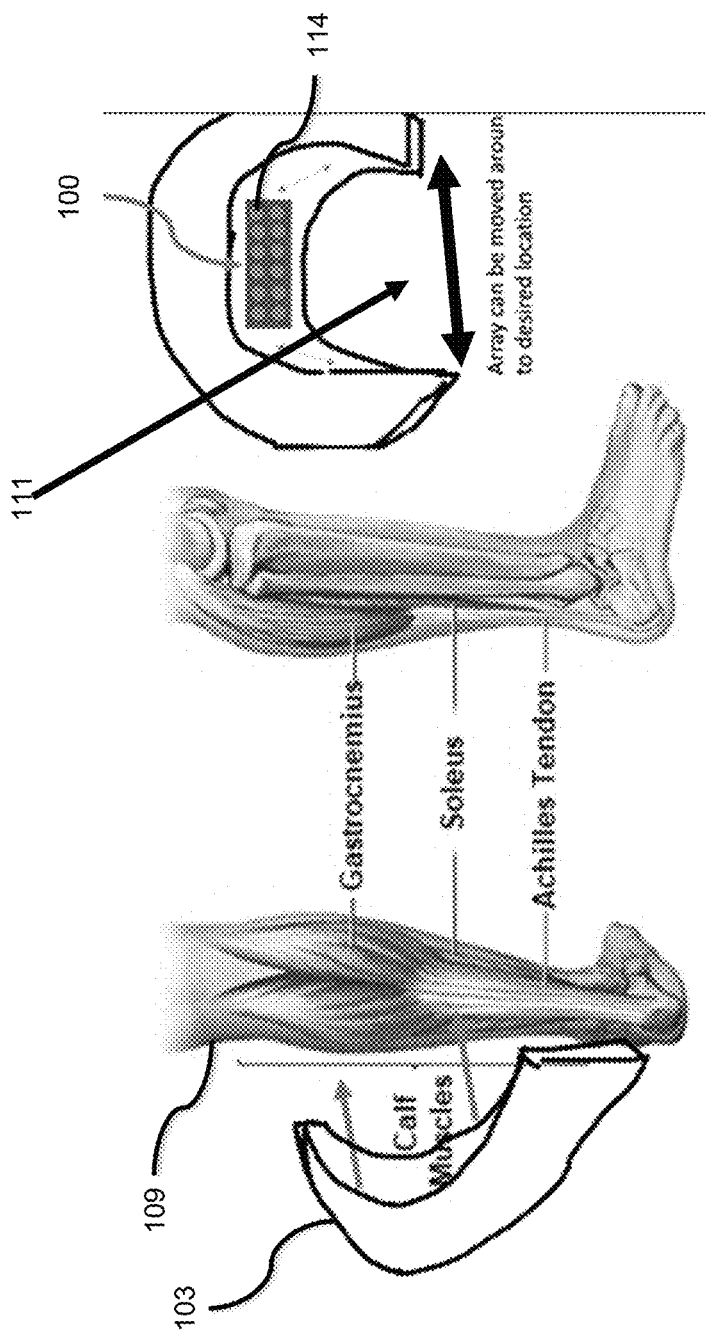
FIG. 2 illustrates a perspective view of the wearable structure that allows the ultrasound therapy device to fit around the lower limb of the user, in accordance with one embodiment of the present disclosure.

FIGS. 1A and 1B illustrates example embodiments of a wearable structure 103 as well as example embodiments of ultrasound therapy device 100. FIG. 1A shows a form factor of wearable structure 103 to secure the ultrasound therapy device 100 around the kidney region, or the lung region 105 of the user 107. FIG. 1B depicts another form factor of wearable structure 103 to secure the ultrasound therapy device 100 around the midsection of user 107 such as the stomach, diaphragm, or appendix. FIG. 2 illustrates a perspective view of the wearable structure 103 that allows the ultrasound therapy device 100 to be secured around the lower limb 109 of the user 107, in accordance with one embodiment of the present disclosure. FIG. 2 is explained in conjunction with FIGS. 1A and 1B.

The wearable structure 103 is securable to a user to hold the ultrasound therapy device 100 against the user's body to transmit the ultrasound to a target therapy area of a user including at least one of a kidney region, a lung region, and a lower limb of the user. The wearable structure 103 allows the ultrasound therapy device 100 to be "worn" or otherwise "adhered" to the user's body. In an embodiment, the wearable structure 103 can be in the form of a vest, or a belt/band that goes around the waist and/or around a lower limb region of the user (e.g., around the leg).

The wearable structure 103 includes a tightening mechanism 111 to adjust the tightness of the wearable structure 103 until it is snug around the chest, waist, and/or around the lower limb region of the user to prevent unnecessary movement of the ultrasound therapy device 100. In an embodiment, the tightening mechanism 111 includes but is not limited to a rubber tension or compression band with adjustable tightness, and an elastic strap with adjustable tightness. Additionally or alternatively, the tightening mechanism can include hook and loop fasteners, buttons, zippers, or other known garment/clothing/medical device technologies that can be used to secure the wearable structure 103 and the ultrasound therapy device 100 in the correct positioning.

The ultrasound therapy device 100 includes a grouping 119 of ultrasound transducer units 113. The ultrasound transducer units 113 are attachable and repositionable in wearable structure 103 to generate and deliver the ultrasound to the target region. The ultrasound transducer units 113 are arranged in an array. The array of ultrasound transducer units 113 is mechanically moved within the wearable structure 103 and is in contact with a material to facilitate penetration of ultrasound into the user's body.

Figure 3:
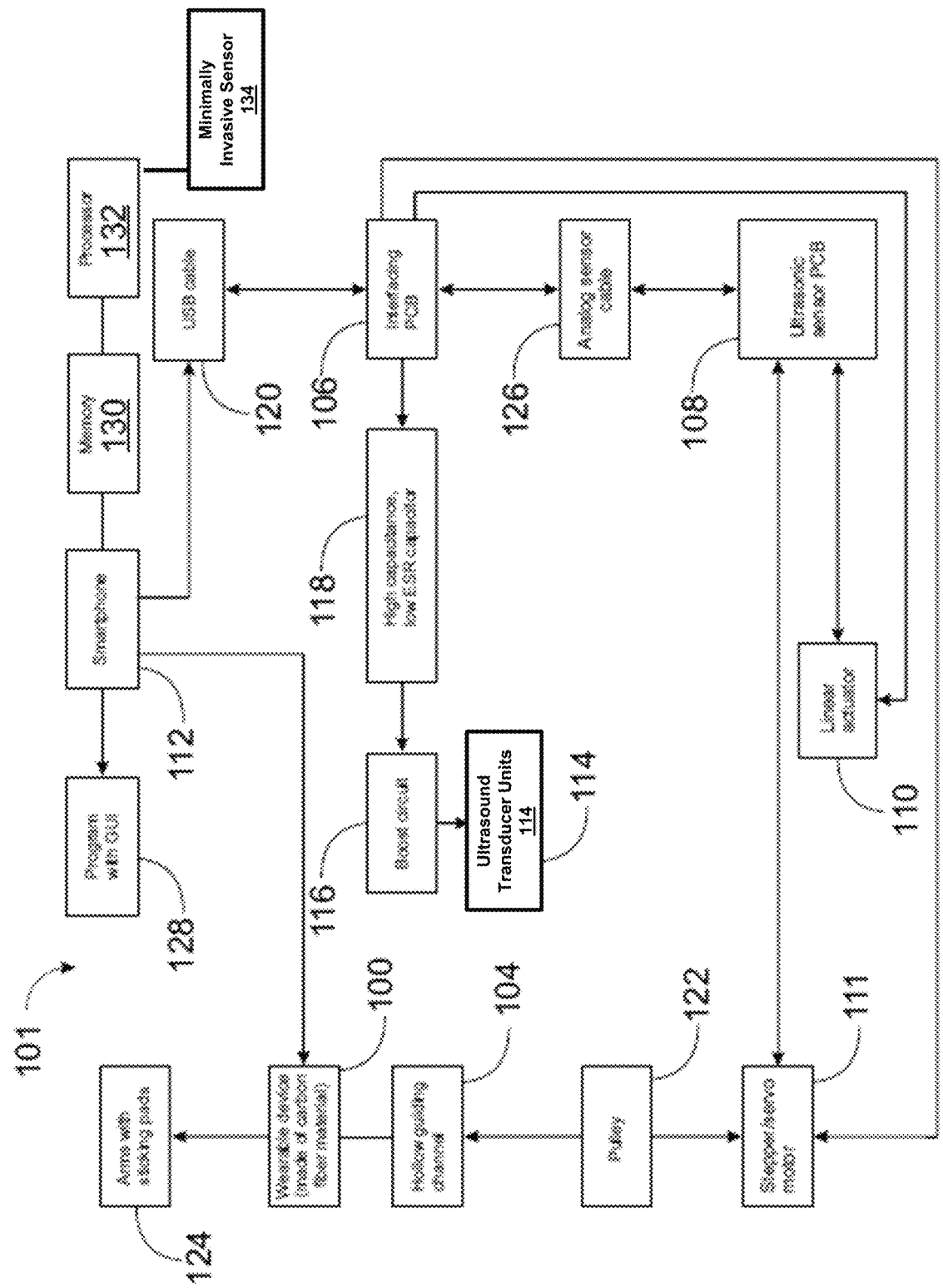
FIG. 3 illustrates a block diagram of example connections between the various components of the wearable structure configured to fit around one or more of: the kidney region, the lung region, and the lower limb of the user, in accordance with one embodiment of the present disclosure.

FIG. 3 illustrates a block diagram of the connections between the various components of the wearable structure configured to fit around one or more of: the kidney region, the lung region, and the lower limb of the user, in accordance with one embodiment of the present disclosure. FIG. 3 is explained in conjunction with FIGS. 1A and 1B and FIG. 2. The ultrasound therapy device 100 includes various ultrasound transducer units 114, a pressure sensor 133, a memory 130, and a processor 132. According to an embodiment herein, the ultrasound therapy device 100 includes a guiding channel 104, an ultrasonic sensor 108, a micro linear actuator 110, and a servo motor 111. The wearable structure 103 (as shown in FIGS. 1A and 1B and FIG. 2) is securable to the user to transmit the ultrasound to a target therapy area of a user including at least one of a kidney region, a lung region, and a lower limb of the user. In some embodiments, the ultrasound therapy device 100 acts as a gadget for the handheld computing device. Examples of the gadget include but are not limited to a casing, a cover, a housing, or an electrical housing. In some embodiments, the ultrasound therapy device 100, or at least the housing/body thereof, is made of carbon fiber material. Examples of handheld computing devices 112 include but are not limited to a computing device, smartphone, mobile device, phablet, tablet, etc. The ultrasound transducer units 114 are attachable and repositionable in the wearable structure 103 to generate and deliver the ultrasound to the target region. The ultrasound transducer units 114 are arranged in an array. The array of ultrasound transducer units 114 is mechanically moved within the wearable structure 103 and is in contact with an impedance matching material, gel, or fluid 300 such as ultrasound gel to facilitate penetration of ultrasound into the user's body. The pressure sensor 133 measures the proximity of the ultrasound transducer units 114 to the user's skin to determine adequate adhesion to the user's skin to facilitate ultrasound tissue penetration.

The ultrasound therapy device 100 is connected to at least one minimally invasive physiological sensor to collect the health status data of the user. In an embodiment, the minimally invasive physiological sensor is selected from the group of minimally invasive sensors 134.

The memory 130 includes ultrasound therapy instructions. The memory 130 is communicatively coupled to the processor 132. The memory 130 stores ultrasound therapy instructions executed by the processor 132. The memory 130 may be a non-volatile memory or a volatile memory. Examples of nonvolatile memory may include, but are not limited to flash memory, a Read Only Memory (ROM), a Programmable ROM (PROM), Erasable PROM (EPROM), and Electrically EPROM (EEPROM) memory. Examples of volatile memory may include but are not limited to Dynamic Random-Access Memory (DRAM), and Static Random-Access memory (SRAM).

The processor 132 processes the ultrasound therapy instructions. The processor 132 may include at least one data processor for executing program components for executing user- or system-generated requests. Processor 132 may include specialized processing units such as integrated system (bus) controllers, memory management control units, floating-point units, graphics processing units, digital signal processing units, etc. Processor 132 may include a microprocessor, such as AMD® ATHLON® microprocessor, DURON® microprocessor OR OPTERON® microprocessor, ARM's application, embedded or secure processors, IBM® POWERPC®, INTEL'S CORE® processor, ITANIUM® processor, XEON® processor, CELERON® processor or other line of processors, etc. Processor 132 may be implemented using a mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc.

Processor 132 may be disposed of in communication with one or more input/output (I/O) devices via an I/O interface. I/O interface may employ communication protocols/methods such as, without limitation, audio, analog, digital, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMAX, or the like), etc.

The processor 132 is configured to transmit the health status data to a server 129 over a network. Network may be a wired or a wireless network, and the examples may include but are not limited to the Internet, Wireless Local Area Network (WLAN), Wi-Fi, Long Term Evolution (LTE), Worldwide Interoperability for Microwave Access (WiMAX), and General Packet Radio Service (GPRS).

The server 129 is configured to analyze the collected health status data to obtain the detected results and transmit them to the computing device over the network for a presentation. Various examples discussed herein refer to one or more servers. As used herein, a "server" is any server computer capable of performing functions stored in a computer-readable storage medium of the server computer. The server computer may download the program code to the processor for use on the computing devices, client computers, or electronic devices.

The ultrasound therapy instructions comprising: determining a non-acute health status of the user based on health status data of the user received by the ultrasound therapy device 100 from a minimally invasive physiological sensor; receiving ultrasonic data from the ultrasound transducer units 114; determining a location of the array of ultrasound transducer units 114 on the user's body; transmitting ultrasound therapy information to the one or more ultrasound transducer units 114; and generating ultrasound therapy in a target therapy area of the user, after a non-acute health state of the user and correct location of the array has been established. In an embodiment, the ultrasound therapy information includes at least one of frequency, temporal average, duty cycle, and therapy duration. In an embodiment, the ultrasound therapy information is configured to induce pulmonary rehabilitative effects. In an embodiment, the ultrasound therapy information is configured to promote one or more of angiogenesis, reduce inflammation, improve renal fibrosis and tubular injury, neovascularization, and ameliorating inflammatory processes. In an embodiment, the ultrasound therapy information includes but is not limited to location data, frequency data, spatial average temporal average data, duty cycle data, and therapy duration data.

In an embodiment, the ultrasound therapy device 100 includes a minimally invasive sensor 134 for minimally invasively acquiring one or more of: pulmonary function information, renal function information, peripheral arterial function, and deep vein thrombosis (DVT) function information of the user. In an embodiment, the acoustic sensor is facing away from the user's skin to enable the detection of environmental acoustic disturbances that could interfere with receiving and sending signals. In an embodiment, the pulmonary function information comprises one or more minimally invasive data from the lungs and self-reported pulmonary health data. In an embodiment, the renal function information comprises one or more minimally invasive data from the kidney and self-reported kidney health data. In an embodiment, the deep vein thrombosis (DVT) function information comprises one or more minimally invasive data from the lower limb and self-reported lower limb health data.

In an embodiment, the processor 132 is configured to receive pulmonary function information, and transmit ultrasound therapy information to the one or more ultrasound transducer units 114 for generating ultrasound therapy. In an embodiment, the processor 132 is configured to receive renal function information, and transmit ultrasound therapy information to the one or more ultrasound transducer units 114 for generating ultrasound therapy. In an embodiment, the processor 132 is configured to receive deep vein thrombosis (DVT) function information, and transmit ultrasound therapy information to the one or more ultrasound transducer units 114 for generating ultrasound therapy.

In an embodiment, the ultrasound therapy is administered in one or more patients diagnosed with one or more of bronchitis, Chronic Obstructive Pulmonary Disease, Cystic Fibrosis, Emphysema, Idiopathic Pulmonary Fibrosis, flu, lung cancer, obstructive sleep apnea, pleurisy, Tuberculosis, pulmonary congestion, kidney diseases, and peripheral artery disease.

In an embodiment, the ultrasound therapy device 100 includes a circuit board (PCB) 106 to connect the one or more ultrasound transducer units 114, the proximity sensor(s), the minimally invasive sensor(s) 134, the positioning mechanism, the processor 132, or pressure sensors. In an embodiment, the proximity sensor is a pressure sensor for measuring the pressure that the one or more ultrasound transducer units 114 apply on the user's skin. The pressure sensors are configured to measure the proximity of an ultrasound transducer to the user's skin. The pressure sensors may include any instruments or devices that translate the magnitude of a physical pressure being exerted onto the sensor into an output signal that can be used to establish a quantitative value for the pressure. Pressure sensors may include but are not limited to potentiometric pressure sensors, inductive pressure sensors, capacitive pressure sensors, piezoelectric pressure sensors, strain gauge pressure sensors, variable reluctance pressure sensors, aneroid barometer sensors, Manometer Sensors, Bourdon Tube Pressure Sensors, Vacuum Pressure Sensors, Sealed Pressure Sensors.

In an embodiment, the ultrasound therapy device 100 includes an inertial measurement unit (IMU) sensor 115 configured to determine whether the ultrasound therapy device 100 is correctly positioned on the user's skin and/or determines user movement.

In an embodiment, the PCB 106 further includes the ultrasonic sensor 108 which is connected to the circuit board (PCB) 106 via an analog sensor cable 126. In an embodiment, the ultrasonic sensor 108 includes a MEMS ultrasonic sensor. In an embodiment, the ultrasonic sensor 108 is a piezoelectric ultrasonic sensor. The PCB 106 can refer to a printed wiring board, printed wiring card, or a printed circuit board (PCB) that mechanically supports and electrically connects electrical or electronic components of the presently disclosed device using conductive tracks, pads, and other features etched from one or more sheet layers of copper laminated onto and/or between sheet layers of a non-conductive substrate.

In an embodiment, the ultrasound therapy device 100 includes a housing for accommodating at least a part of one or more ultrasound transducer units 114, the proximity sensor, and the processor 132.

In an embodiment, the processor 132 is configured to analyze one or more of the pulmonary function information, the renal function information, and/or the deep vein thrombosis (DVT) function of one or more of the lung, the kidney, and the lower limb of the user and determine one or more locations on the lung the kidney and the lower limb of the user where the one or more of the ultrasound signals are focused based on ultrasonic sensor data of the one or more ultrasound transducer units 114.

In an embodiment, the circuit board is a PCB 106 is connected to one or more of: an analog-to-digital converter (ADC) for converting analog ultrasonic data into digital data; a micro-controlling unit with a power and data transmission port; one or more large bandwidth operational amplifiers circuits; a plurality of digital buffers; at least two signal mixers for precise doppler calculation; a plurality of filters suitable for an operating range of a piezoelectric ultrasonic sensor; a plurality of bidirectional drivers for a micro linear actuator and a servo motor; and a plurality of headers and a plurality of PWM lines to provide the power to the micro linear actuator and the servo motor.

In an embodiment, the ultrasound therapy device 100 includes a boost circuit 116 for providing power feed to the one or more ultrasound transducer units 114. In an embodiment, the boost circuit 116 comprises a low equivalent series resistance (ESR) capacitor and utilizes an accumulated charge on high capacitance.

In an embodiment, the array is configured to direct the ultrasound beam to the one or more regions of the lung, the kidney, and the lower limb and execute the ultrasound therapy information in the one or more regions.

In an embodiment, the ultrasound therapy device 100 is configured to compare the pulmonary or renal health of the user in the one or more regions over time to determine the efficacy of the ultrasound therapy. In an embodiment, the ultrasound therapy device 100 is configured to update the ultrasound therapy based on the observed efficacy of the ultrasound therapy over time. In an embodiment, the ultrasound therapy device 100 is configured to create a map of the user's lungs, kidneys, and lower limbs. In an embodiment, the ultrasound therapy device 100 is configured to collect information on the user's health condition through a questionnaire and/or patient health database.

In an embodiment, the ultrasound therapy device 100 includes a pressure adjustment mechanism configured to adjust the tightness of the ultrasound transducer units 114 to the user's skin. In an embodiment, the ultrasound therapy device 100 receives power through a cable from an external electric power system.

Often used with the device is an impedance matching material, gel, or fluid 300 to facilitate the ultrasound therapy device's contact with the skin, help steer the ultrasound to the target therapy area and prevent dispersion or other loss of the waves. In an embodiment, the ultrasound therapy device 100 includes impedance matching material, gel, or fluid 300 or is used with a removable ultrasound gel patch that is connected to the skin-facing side of the ultrasound therapy device 100. In another embodiment, the ultrasound therapy device 100 is used with ultrasound gel.

The ultrasound transducer units 114 are attached to the PCB 106 via a spring-based mechanism to generate ultrasounds. The pressure sensors measure the proximity of the ultrasound transducer units 114 and/or the ultrasonic sensor 108 to the skin. The ultrasonic sensor 108 is configured to detect different regions of the user's organ and determine a location on the chest where the ultrasound transducer units 114 are placed. The micro linear actuator 110 is attached to the ultrasonic sensor 108 to acquire Pulse Width Modulation (PWM) control from the interfacing circuit board 106. The micro linear actuator 110 is configured to place the ultrasonic sensor 108 on the skin of a user to obtain analog data with a sticking force chosen to minimize an error resulting from pressing the skin with the ultrasonic sensor 108.

In some embodiments, the ultrasound transducer units 113 operate with a spring-ball detent system or the equivalent. This helps the ultrasound therapy device 100 push the individual ultrasound transducers against the skin especially if the skin is not flat. The system is optionally designed to prevent lateral movement of the ultrasound transducer units.

The servo motor 111 is attached to the micro linear actuator 110 to acquire the PWM control from the interfacing circuit board 106 via a bidirectional PWM driver on the interfacing circuit board 106. In some embodiments, the micro linear actuator 110 includes a static side and a moving stroke and is attached to the servo motor 111 from the static side, and the ultrasonic sensor 108 is attached to the moving stroke of the micro linear actuator 110. In some embodiments, the pressure sensors, the ultrasound transducer 114, and the piezoelectric ultrasonic sensor 108 is soldered to slim printed circuit board (PCB) 106.

In some embodiments, the servo motor 111 moves in a plurality of channels created in the body of the ultrasound therapy device 100. In some embodiments, functions of the servo motor 111 may be performed by a stepper motor. The servo motor 111 is powered and controlled by the interfacing circuit board (PCB) 106. In some embodiments, the servo motor 111 is attached to the micro linear actuator 110 to acquire the PWM control from the interfacing circuit board 106 via a bidirectional PWM driver placed on the interfacing circuit board 106. In some embodiments, the hollow guiding channel 104 is built into the body of the ultrasound therapy device 100 to guide and restrict the movement of the servo motor 111.

In some embodiments, the interfacing circuit board (PCB) 106 is connected to the handheld computing device 112 via a power and data transmission cable 120 with data and power lines. The power and data transmission cable 120 receives power from the handheld computing device 112.

In some embodiments, the ultrasound transducer 114 obtains power feed from a boost circuit 116. In some embodiments, the boost circuit 116 utilizes an accumulated charge on high capacitance and a low equivalent series resistance (ESR) capacitor 118. The accumulated charge is acquired from the handheld computing device 112 via the power and data transmission cable 120 during idle time.

In some embodiments, ultrasound therapy device 100 includes a pulley 122 attached to the servo motor 111 to move the ultrasound transducer unit inside the hollow guiding channel 104 in the body of the ultrasound therapy device 100. In some embodiments, the ultrasound therapy device 100 includes a plurality of arms with fixation pads 124 are attached to the bottom of the housing 102 allowing the gadget or device 100 to be attached to the user's skin.

In some embodiments, the ultrasound therapy device 100 is powered by the handheld computing device 112 or may obtain power from an external battery that can supply electrical power to the PCB 106. The external battery can be based on Lithium Polymer (Li-Poly) and Lithium-Ion (Li-Ion). Furthermore, the battery can be operated by a power management integrated circuit such as power MOSFETs. Alternatively, the ultrasound therapy device 100 can be powered by a handheld computing device. In one embodiment, the ultrasound therapy device 100 can be powered by a power source, where the power source can be one or batteries, AC mains, an inductive power transfer with no physical contact, where the inductive power transfer is powered by e.g. AC mains, fiber optic power supply, where the fiber optic power supply can e.g. comprise an optical-to-electrical converter, like a solar cell, for providing electrical energy, a solar array for providing electrical energy, a wind-up manual system for providing electrical energy e.g. by an electrical generator driven by the wind-up manual system, or an energy-harvesting system for providing electrical energy from a magnetic field. In the embodiment where inductive power transfer relies upon an AC main, the ultrasound therapy device 100 may comprise a filter to shunt power transients of high frequency and/or large magnitude.

To avoid any measurement error caused by the weight of the measurement device, a hollow housing made from carbon fibers similar to that of the handheld computing device can be used to create a hollow space around the sensor to guarantee there is no extra weight from the ultrasound therapy device 100 on the skin between the sensor and artery, and thus guarantee precise results, so the pressure applied to the skin by the ultrasound therapy device 100 is exerted at points far from the artery and has no effect on the artery diameter or shape.

A great advantage of employing handheld computing device technologies is to provide cheap and reliable access to pulmonary function, renal function, peripheral arterial function, and deep vein thrombosis (DVT) function measurement, and add the feature of an ultrasound to harness the thermal and non-thermal effects of high-intensity focused ultrasound (HIFU) and ultrasounds to treat organ failure, for relief and mobility restoration. The ultrasound therapy device 100 can work with automated precision sensor positioning and negligible error of the sensor weight.

The individual transducer units 114 can be phase shifted with respect to each other. Depending on the relative phase shift between the transducer units, the position of the maximum of the total superposition wave at a plane with respect to the 1D or 2D array can be positioned by adjusting the phases for each of the transducer units in the array. Using this method, the ultrasound can be steered to a specific angle (and position) without using any moving mechanical parts. Likewise, the ultrasound waves from the transducer units can be focused at a certain area of the organ, and the ultrasound can be controlled regarding angle and focus on the organ. In an embodiment, the array can be one-dimensional or two-dimensional. If the array is one-dimensional, the generated ultrasounds can be controlled in one dimension. If the array is two-dimensional, the generated ultrasounds can be controlled in two dimensions. In an embodiment, the at least one array of ultrasound transducer units can be configured to generate electric signals as responses to reflected ultrasound waves from the kidneys, lungs, and limbs. That the transducer units can be two-way transducers means that the array of ultrasound transducer units can generate in addition to the ultrasounds for treating kidney disease, peripheral artery disease, and deep vein thrombosis also generate ultrasound waves and register the reflected ultrasound waves for generating a picture of the kidneys, lungs, and limbs and even a moving picture of the kidneys, lungs, and limbs.

When the reflected ultrasound waves enter the array of ultrasound transducer units the reflected ultrasound waves create voltage/current responses from the ultrasound transducer units depending on the strength of the amplitude of the vibrations/pressure wave. This means that the array of ultrasound transducer units can be used as an active sensor array for monitoring the status of the organ. Since the reflected ultrasound waves will reach the different transducer units at different times, the array of ultrasound transducer units can register the phase difference and build a picture of the organ based on the reflected ultrasound waves. The array of ultrasound transducer units can be used to localize the organ in the extrapolated actuator/sensor array plane by using the amplitude and time delay between each sensor/actuator in the array.

In general, a controller sends electrical signals for controlling the ultrasound transducer units, where the electrical signals are converted to ultrasound waves. Phased array systems are composed of an array of transducer units in 1D or 2D arrays and can transmit waves independently at different times or phase changes between the transducer units. To focus or to steer the ultrasound waves, time delays or phase changes are applied to the ultrasound transducer units to create constructive interference of the wavefronts of the ultrasound wave from each ultrasound transducer unit. Due to this effect, the ultrasound wave can be steered to a certain angle, and/or the energy can be focused on any position of the kidneys, lungs, and limbs.

After transmitting the ultrasound waves, the ultrasound transducer units receive the reflected ultrasound waves from the organ as an echo, as well. By having the ultrasound transducer units to be used inversely, the ultrasound transducer units can convert the received reflected ultrasound waves into electrical signals that can be registered by the controller. In the same way, the array of ultrasound transducer units can steer and focus the generated ultrasound waves as mentioned above, and the array of ultrasound transducer units can determine the direction and origin of the reflected ultrasound waves. All received waves are converted to electrical signals and can be evaluated by signal analysis to obtain the health status of the kidneys, lungs, and limbs and/or the effectiveness of the transmitted ultrasound to the kidneys, lungs, and limbs.

The advantages of phased array systems like the array of ultrasound transducer units include the ability to perform scanning of the ultrasound waves, which reduces inspection times by eliminating or reducing the need to mechanically move the array of ultrasound transducer units.

When the array of ultrasound transducer units 114 is used for generating an image of the organ the energy level of the generated ultrasound waves may be lower or much lower than 0.02 20 $mJ/mm^2$.

Since the ultrasound waves have a frequency above 20 kHz, the acoustic transducer, like a microphone or an accelerophone, only sensitive to sound waves below 20 kHz or below 15 kHz will not be able to register the ultrasound.

The acoustic sensor can preferably be sensitive within the range of 3-20 kHz, preferably within the range of 4-20 kHz, and most preferably within the range of 5-20 kHz.

Figure 4:
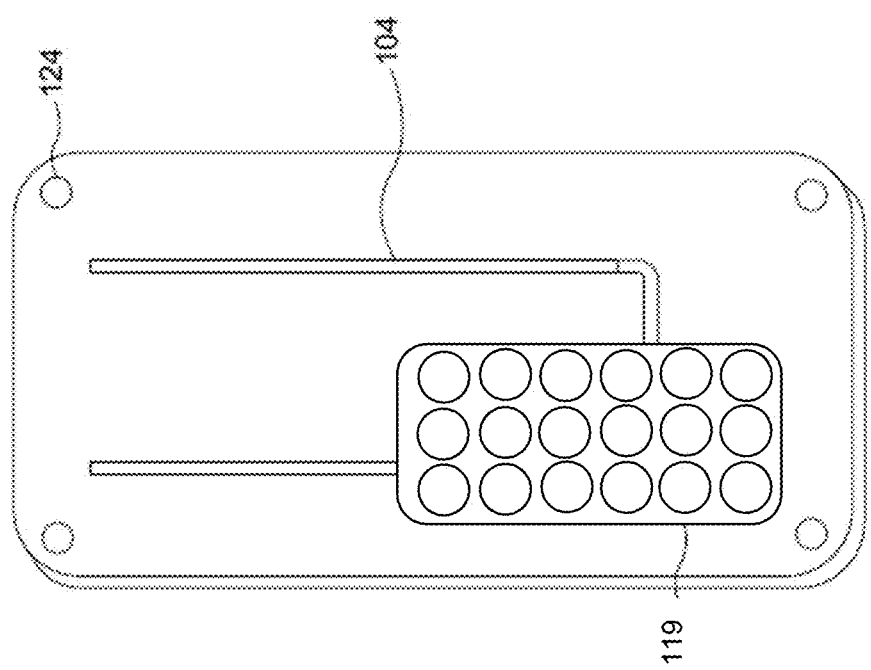
FIG. 4 illustrates a bottom view of an example ultrasound therapy device, in accordance with one embodiment of the present disclosure.
Figure 5:
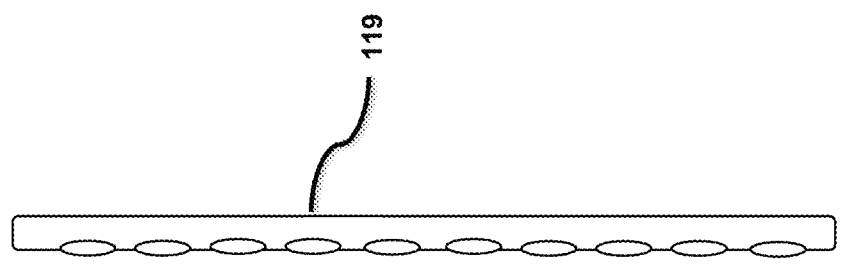
FIG. 5 illustrates a side view of the ultrasound therapy device, in accordance with one embodiment of the present disclosure.

FIG. 4 illustrates a bottom view of the ultrasound therapy device 100, in accordance with one embodiment of the present disclosure. FIG. 4 is explained in conjunction with FIG. 3. The arms with fixation pads 124 are configured to be placed on the body of the patient. The hollow guiding channel 104 is placed into the body of the ultrasound therapy device 100 to guide the ultrasound transducer unit 114 via movement of the stepper motor or servo motor 111 and the linear actuator 110 and PCB 106 of the ultrasonic sensor 108 attached to it. According to an embodiment herein, the guiding channel 104 is placed into the body of the ultrasound therapy device 100. The guiding channel 104 is configured to position the soundwave transducer unit within a target therapy area of the user. The PCB of the ultrasonic sensor 108 is attached to the stepper motor 111 via the linear actuator 110. FIG. 5 illustrates a side view of the ultrasound therapy device 100, in accordance with one embodiment of the present disclosure.

Figure 6:
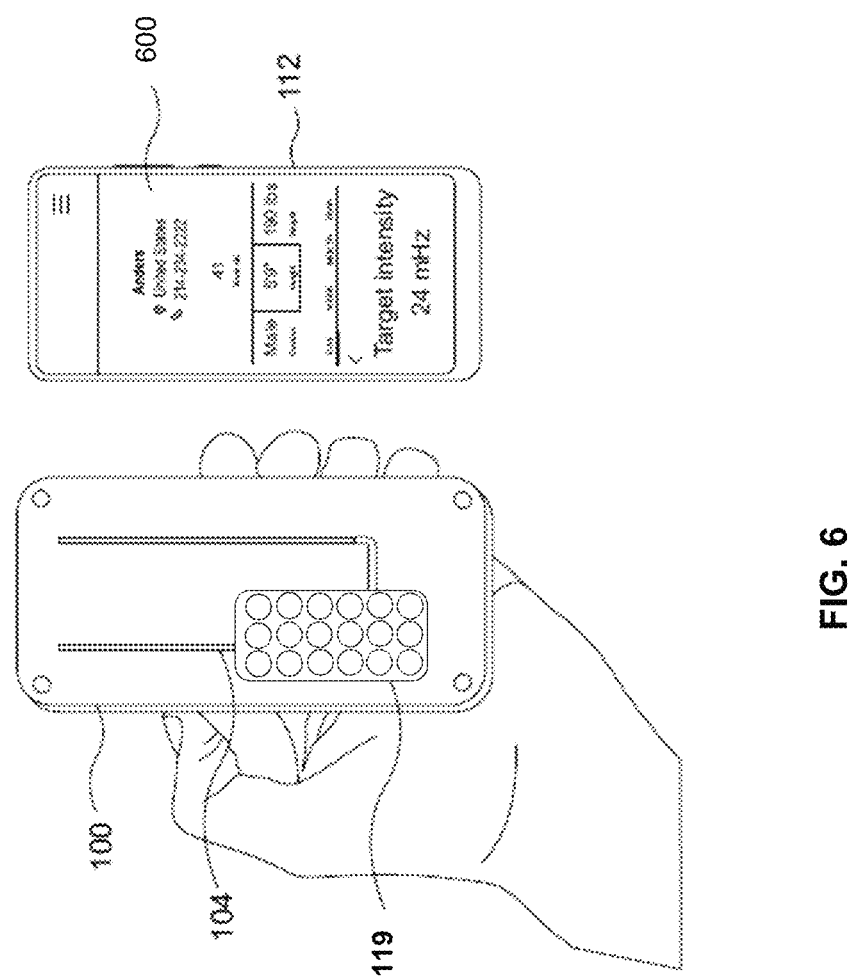
FIG. 6 illustrates a monitoring application installed within the ultrasound therapy device in the form of a handheld computing device, in accordance with one embodiment of the present disclosure.

FIG. 6 illustrates a monitoring application 600 installed within the handheld computing device 112, in accordance with one embodiment of the present disclosure. FIG. 6 is explained in conjunction with FIG. 3. The monitoring application 600 may be based on one or more operating systems comprising Android®, and iOS®. The ultrasound therapy device 100 requires the user to register on the monitoring application 600 installed or configured within the handheld computing device 112. Memory 130 is configured to register the user over the monitoring application 600 by receiving one or more credentials from the user for providing access to the monitoring application 600.

Examples of the credentials include but are not limited to a username, password, age, gender, phone number, email address, location, etc. In some embodiments, the monitoring application 400 is commercialized as a software application or a mobile application, or a web application for health assessment. A user may include a patient, a patient using the monitoring application using the handheld computing device 112 such as those included in this invention, or such a handheld computing device 112 itself. In some embodiments, the monitoring application 600 is a combination of a software program with a graphical user interface (GUI) 205 (shown in FIG. 6) which is running on the handheld computing device 112 to present resulting data such as name, location, age, gender, height, weight, periodical target intensity, etc. and allow the user to do suitable adjustments based on the resulting data. The resulting data is obtained by one or more ultrasonic sensors 108 configured with the ultrasound therapy device 100.

According to an embodiment herein, processor 132 processes the captured/obtained data and transmits it to an external computing device or a server 129 for further processing over a network. The processed data related to the organ's health of the user is presented on the monitoring application 400. The network may be a wired or a wireless network, and the examples may include but are not limited to the Internet, Wireless Local Area Network (WLAN), Wi-Fi, Long Term Evolution (LTE), Worldwide Interoperability for Microwave Access (WiMAX), and General Packet Radio Service (GPRS).

The monitoring application 600 enables the user to continuously monitor the organ function. Further, the monitoring application 600 utilizes machine learning for automatic positioning and determining the intensity of ultrasonic transducers.

Figure 7:
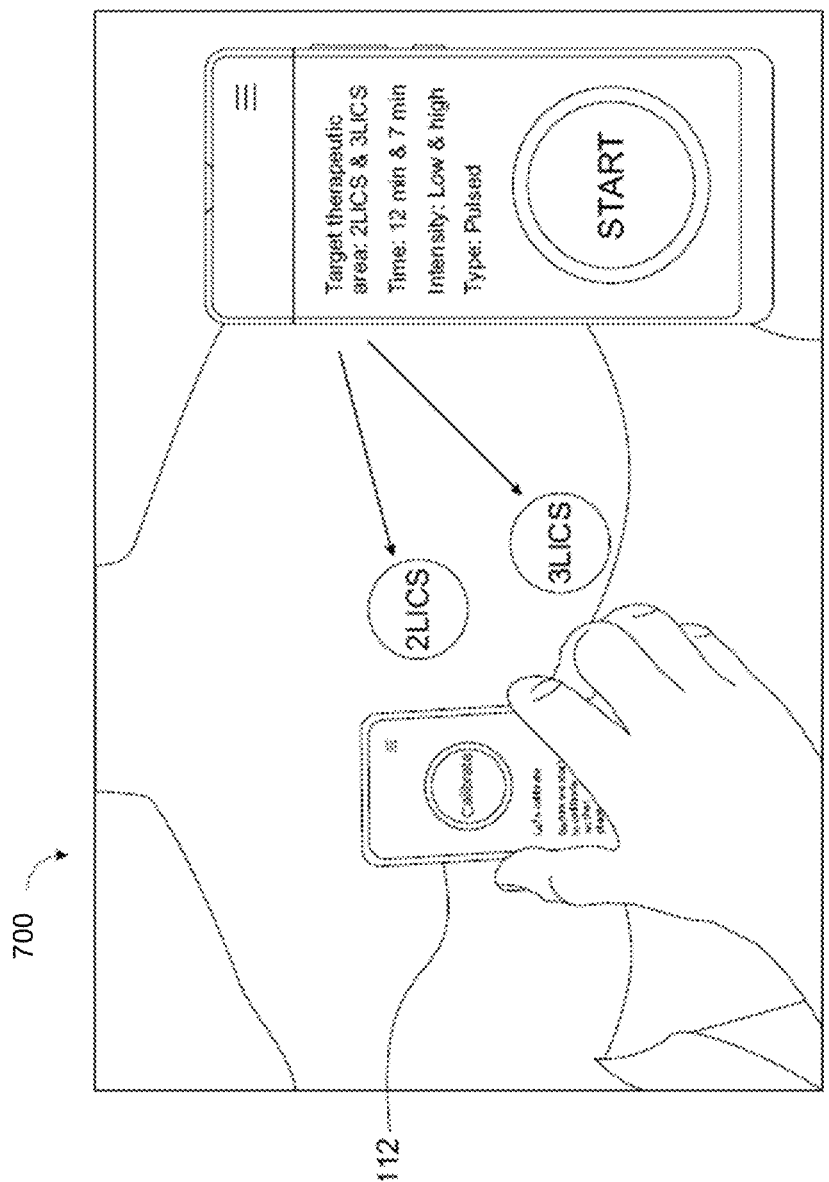
FIG. 7 illustrates a perspective view of the handheld computing device placed against the body or chest of a user, in accordance with at least one embodiment.

FIG. 7 illustrates a perspective view 700 of the handheld computing device placed against the body or chest of a user, in accordance with at least one embodiment. FIG. 7 is explained in conjunction with FIG. 6. The monitoring application 600 directs the user through the GUI 205 to start the measurement of organ function. Then the user places the handheld computing device against his/her chest as shown in FIG. 6. The handheld computing device 112 may have a shape adapted to fit firmly on the target therapy area. The shape of the handheld computing device 112 is a bend or curved so that it perfectly fits on the patient's target therapy area.

In some embodiments, the ultrasonic sensor 108 is combined with the one or more proximity sensors, such as pressure sensors, that allow the linear actuator to place the ultrasound transducer unit 114 and/or the ultrasonic sensor 108 right on the skin with minimum and fixed sticking force to minimize the error resulting from pressing the skin with a probe. According to an embodiment herein, the ultrasound therapy device 100 utilizes a closed-loop control using a digital PID algorithm to ensure that the applied force to the skin doesn't cause additional errors in the measurement process. Further, ultrasound therapy device 100 utilizes the closed-loop control using the digital PID algorithm to ensure that the position of the sensor is optimized automatically to make sure that the applied measurement cannot be optimized further.

In some embodiments, the ultrasonic sensor 108 uses an integrator as a part of ultrasonic calculator circuits. This can be a solution where sampling of the direct output waveform can introduce many problems since the output waveform does not have an exact wave shape, while an integrator allows measurement of the changes by determining the nonlinearity of the resulting waveform from the integrator. Finally, the optional use of analog filters helps to ensure that any noise from external sources is neglected so that the input of the integrator is known to be from the ultrasonic reading rather than ambient EM waves at the integrator input.

Figure 8:
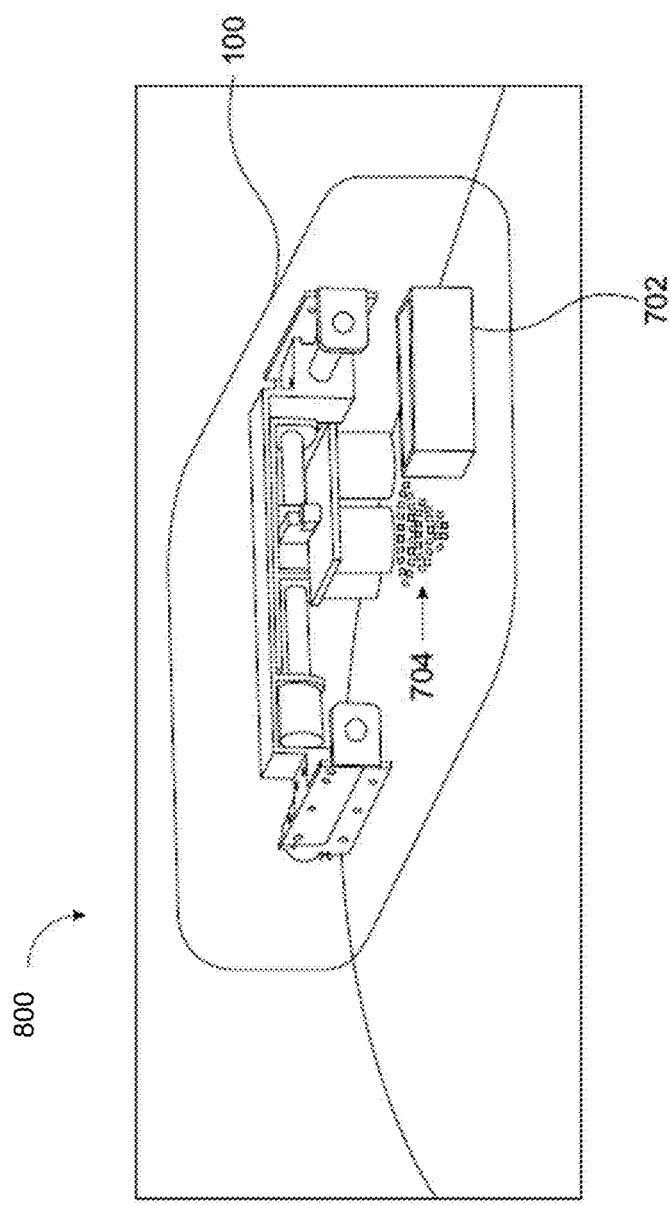
FIG. 8 illustrates a first exploded view of the placement of the ultrasound therapy device against the body of the user, in accordance with at least one embodiment.

FIG. 8 illustrates a first perspective view 800 of the placement of the ultrasound therapy device 100 (transparent) against the body of the user, in accordance with at least one embodiment. According to an embodiment herein, the ultrasound therapy device 100 includes a container 702 to store impedance matching material, gel, or fluid 300. FIG. 8 also depicts an example ultrasound wave 704 generated by the ultrasound transducer units 114.

Figure 9:
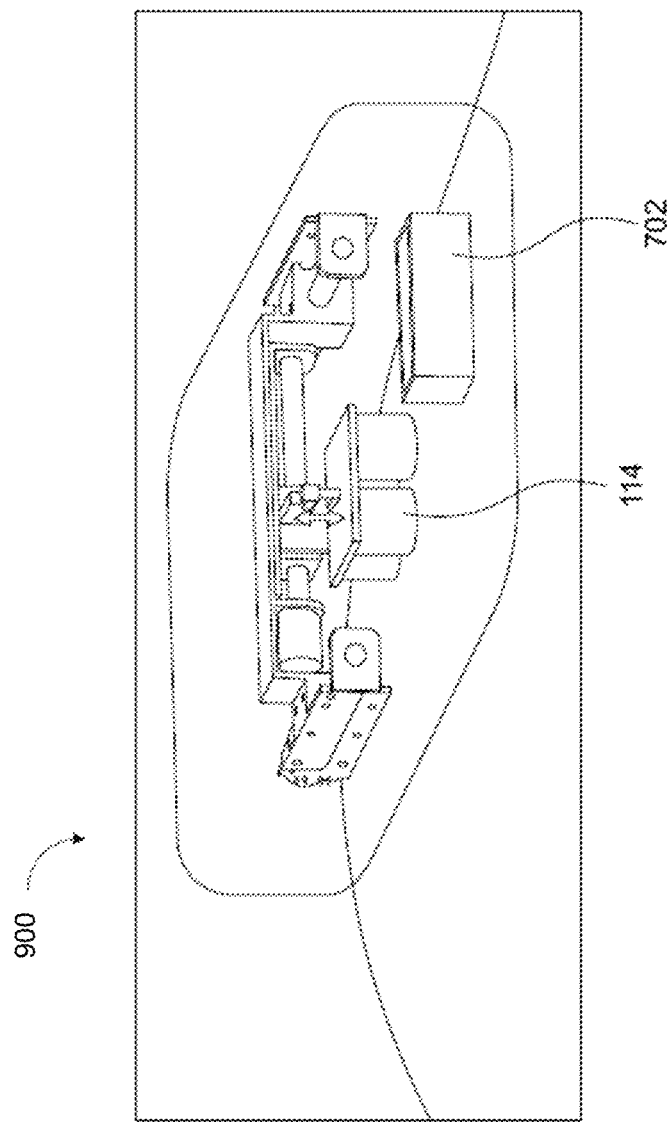
FIG. 9 illustrates a second exploded view of the placement of the ultrasound therapy device against the chest of the user, in accordance with at least one embodiment.

FIG. 9 illustrates a second perspective view 900 of the placement of the ultrasound therapy device 100 (transparent) against the chest of the user, in accordance with at least one embodiment. FIG. 9 is explained in conjunction with FIG. 8. The pulsation frequency and strength of the ultrasound generated by the ultrasound transducer units 114 are directed at suppressing hypertrophic cardiomyopathy and/or myocardial interstitial fibrosis.

Figure 10:
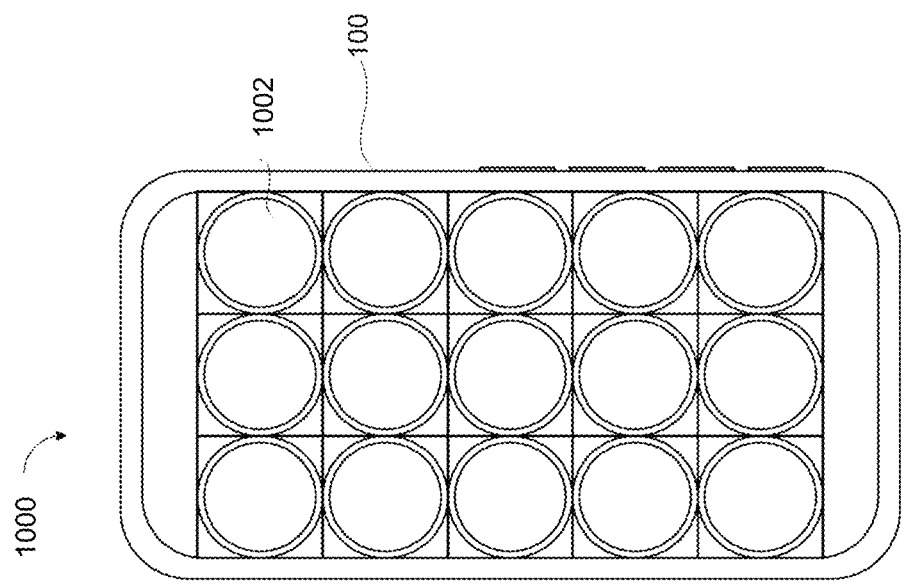
FIG. 10 illustrates a perspective view of a matrix or array of ultrasound transducer units, in accordance with at least one embodiment.

FIG. 10 illustrates a skin-facing side view of an example embodiment of ultrasound therapy device 1000 having a matrix or array of ultrasound transducer units. FIG. 10 is explained in conjunction with FIG. 3. In another embodiment, the ultrasound therapy device 100 of the present ultrasound therapy device 100 includes a matrix of ultrasound transducers 1002 instead of the linear actuators and a guiding channel. According to an embodiment herein, different of the ultrasound transducers 1002 are activated depending on which region of the organ needs treatment. In an embodiment, the ultrasound transducers 114 are activated in accordance with the region of the organ that is to be analyzed and/or treated. The ultrasound transducer units 114 can be adjusted electronically and/or mechanically to ensure a good fit with the user's skin.

In one embodiment, the array of transducer units can be configured to generate ultrasound signals or pulsations for ultrasound therapy and in addition be configured for providing an electrical signal in response to an incoming ultrasound signal or pulse.

Figure 11:
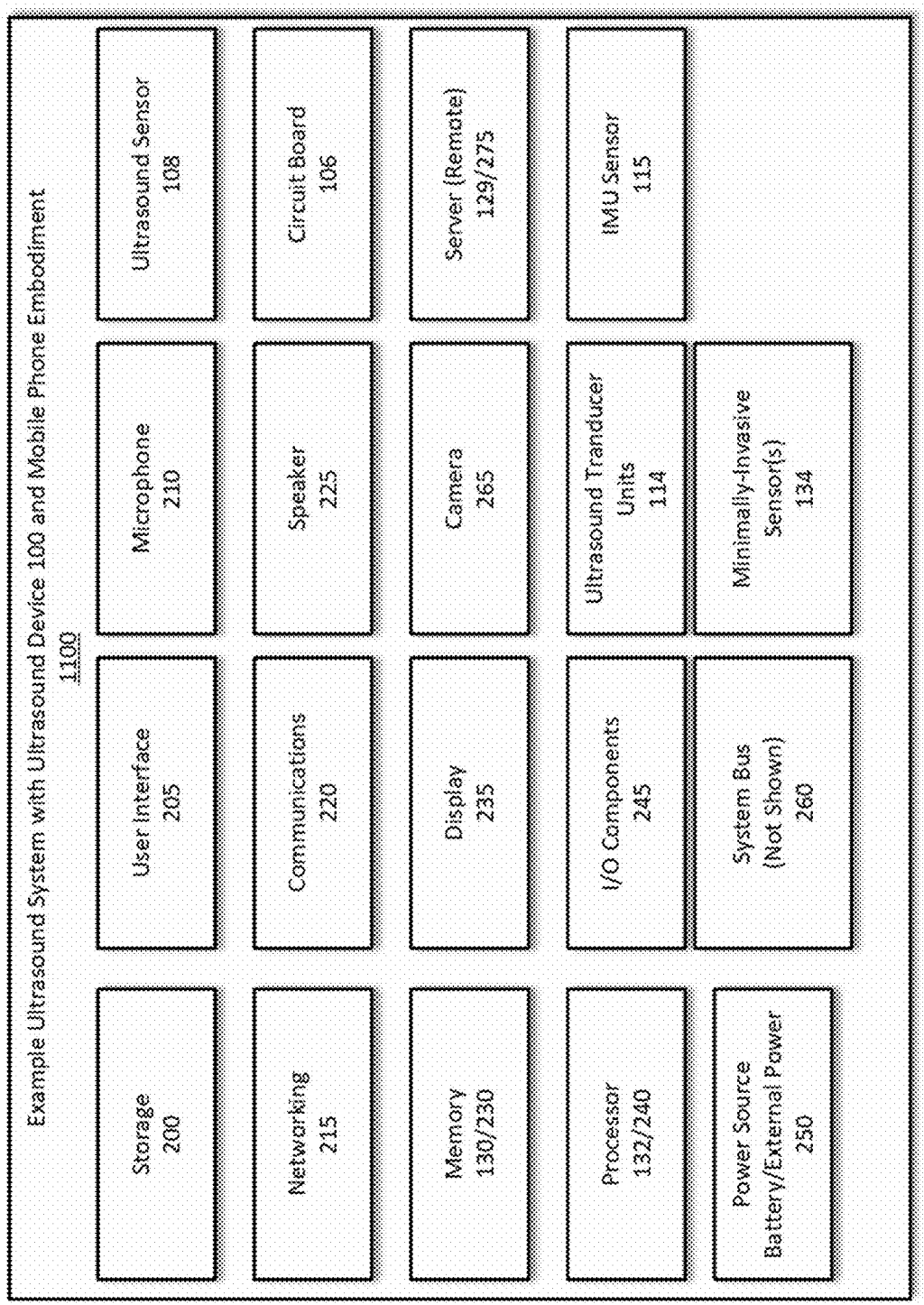
FIG. 11 depicts an example electronics diagram of an example ultrasound system.

FIG. 11 depicts an example electronics diagram of an example ultrasound system 1100. Ultrasound system 1100 includes ultrasound therapy device 100 and a mobile phone (or other handheld device), which lets the ultrasound therapy device have more functionality while using the resources that a user might already have on them. The example mobile phone contains storage 200, User Interface (e.g., a touch screen) 205, Microphone 210, Networking components 215, telephony components 220, speaker 225, Memory 230, touch screen display 235, processor 240, Input/Output (I/O) Components 245, Battery/Power System 250, Camera 255, and System Bus 260 connecting the various components together. The example ultrasound therapy device contains circuit board 106, acoustic sensor 108, ultrasound transducers 114, memory 130, processor 132, minimally invasive sensors 134, ultrasound transducers 114, an optional IMU sensor 115, The listed elements can be on either or both of the ultrasound therapy device or the mobile phone. (This is why some elements are shown with more than one reference numeral.) For example, the processor and memory may be only on the mobile phone and the ultrasound therapy device can take the form of a mobile phone case. Alternatively, the ultrasound therapy device can be integral with the mobile phone. The system with similar components can take other forms and be without a mobile phone. The power source can use batteries and/or external power sources and be on one or both devices. The electrical systems, if needed, could be modified to include the ability to transmit and/or draw significant amounts of power. A server 129/275 could be on one of these devices. Alternatively, the server 129/275 can be remote so that complex computing and calculations could be performed at a location with higher performance capabilities which helps keep the ultrasound therapy device and mobile phone simpler and more economical.

Alternatively, the mobile phone here could be another handheld device like a tablet, laptop, or a smart watch. Additionally or alternatively, it could be separate from or integrated with the ultrasound therapy device.

Figure 12:
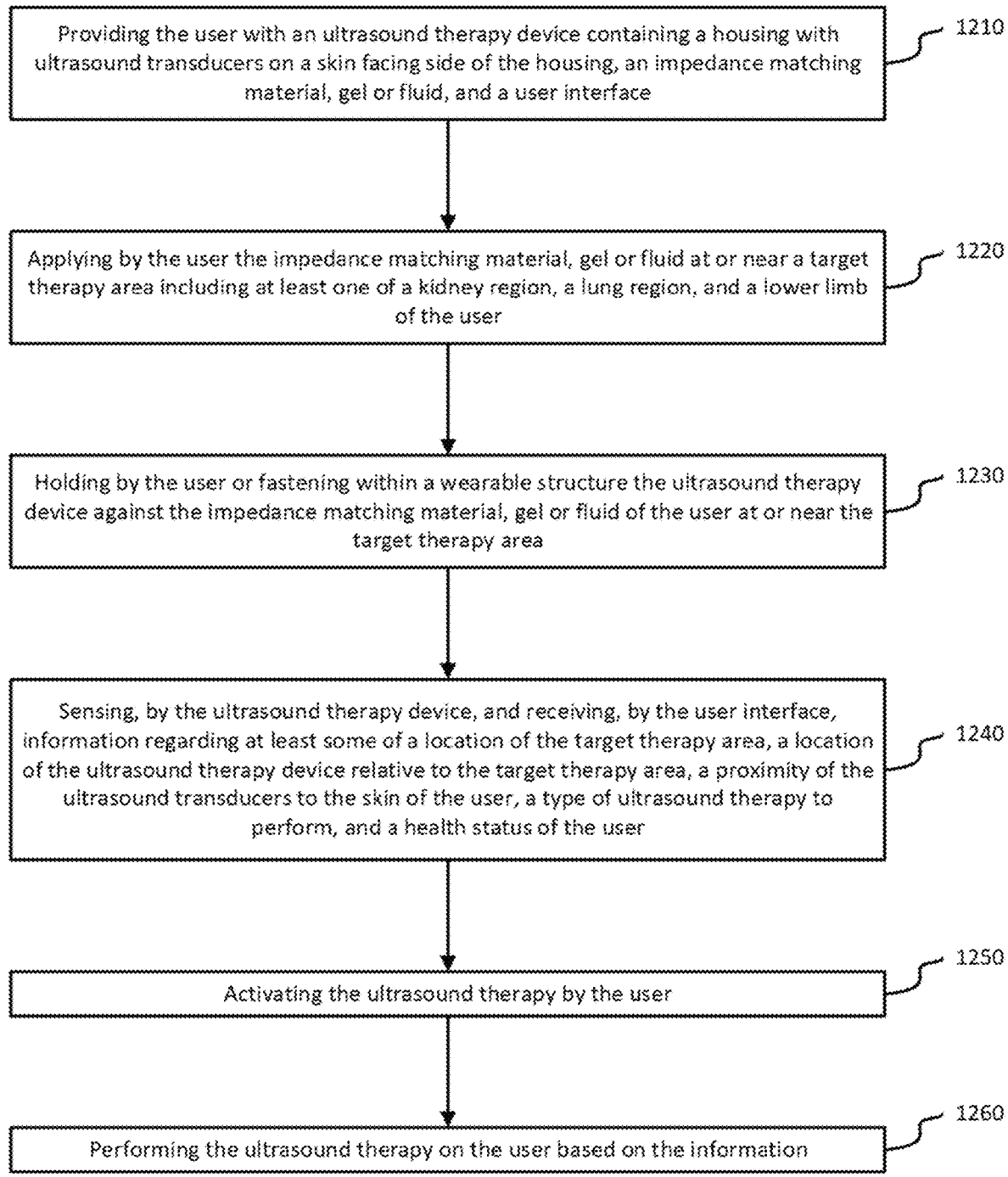
FIG. 12 is a flowchart of an example method of applying automated ultrasound therapy.

FIG. 12 is a flowchart of an example method for applying ultrasound therapy by a user. At step 1210, the user is provided with an ultrasound therapy device containing a housing with ultrasound transducers on a skin facing side of the housing, an ultrasound propagation medium, and a user interface. At step 1220, the user applies the impedance matching material, gel, or fluid 300 at or near a target therapy area including at least one of a kidney region, a lung region, and a lower limb of the user. As mentioned above, this impedance matching material, gel, or fluid 300 could be in the form of ultrasound gel or an ultrasound gel patch or water. At step 1230, either the user holds or wears and fastens a wearable structure that secures the ultrasound therapy device against the ultrasound propagation medium of the user at or near the target therapy area. At step 1240, information regarding at least some of a location of the target therapy area, a location of the ultrasound therapy device relative to the target therapy area, a proximity of the ultrasound transducers to the skin of the user, a type of ultrasound therapy to perform, and a health status of the user is sensed, by the ultrasound therapy device, and/or received, by the user interface. At step 1250, the user activates the ultrasound therapy. At step 1260, the ultrasound therapy device performs the ultrasound therapy on the user based on the information.

The present disclosure further relates to a device configured to provide an automated ultrasound treatment. The user can have access to the sensor data, such as ultrasonic data and/or electronic stethoscope data (and/or other minimally invasive health data of the user) from a plurality of regions of the user. The user can therefore identify the one or more diseases and can analyze the severity of said one or more diseases in one or more regions. This can be done by employing a disease type and severity machine learning model, e.g., classification model trained on clinical gold standards of different health conditions. E.g. a breathing test for pulmonary health, a d-dimer and/or ultrasound assessment of presence of thrombus, kidney function tests such as Glomerular filtration rate (GFR) and peripheral arterial blood flow tests such as an ankle-brachial index and/or a patient self-reported health outcome/wellbeing questionnaire, etc. These tests are not limited to preexisting tests but may comprise any measurements that indicate the efficacy of the ultrasound therapy. Then the user can identify the ultrasound therapy parameters (intensity, duration, and/or pulsation frequency) in one or more regions based on the user's characteristics, e.g. body size, age, type, and/or severity of disease (e.g. tissue stiffness may require an ultrasound therapy to relax the muscle and presence of thrombus may require an ultrasound therapy to destroy thrombus). Lastly, the user can administer the ultrasound therapy based on identified therapy needs.

For the first time usage of the automatic calibration of the ultrasound therapy device to map the location and size of the user's organs the user typically performs various steps. The user can access data of ultrasound sensor data and/or minimally invasive sensor 134 data from a plurality of regions (the data collection regions can be randomized and/or preset). Further, the user can identify the unique markers and/or patterns of each region for example by training a machine learning model to identify each region. Preferably, clustering methods can be used to segment data into different groups/regions. Furthermore, the position data corresponding to positioning of the sensors and/or ultrasound transducer unit for each region can be stored in memory and/or cloud so that data can be accessed at a later point.

For the first time usage, for manually calibrating the ultrasound therapy device to map the location and size of the user's organ, the user may perform various steps. Based on user characteristics (e.g., gender and body size), the device can be navigated to the desired region by a preset formula/decision rule. For example, if the user is female, 55 kg, and 70 years of age—one may position the ultrasound transducer unit in the bottom right quadrant of the device when the disease to treat is located in that region relative to the position of the device.

The presently disclosed device can be configured to harness non-thermal properties of ultrasound therapy to generate stem cell differentiation, angiogenesis, and anti-inflammatory effects, as a treatment for a plurality of diseases including but not limited to ischemia and/or fibrosis. Said non-thermal properties may be achieved through increased pressure and/or amplitude to generate microstreaming (whereby increased fluid movements can promote endothelial shear stress), jetting (whereby vascular permeability can be increased), bubble expansion and/or compression (whereby vascular permeability can be increased).

Specifically, the ultrasound therapy device can be configured to harness thermal effects of ultrasound through increased pulse length and/or power applied by means of the ultrasound transducer unit such that local tissue temperature, which may lead to liquefactive necrosis, can be increased.

Additionally, the ultrasound device can be configured to harness molecular effects. Said molecular effects may include but are not limited to the upregulation of angiogenic factors, increased nitric oxide synthase activity, anti-inflammatory properties, increased differentiation of myocytes, endothelial cells, and/or vascular smooth muscle cells.

The presently disclosed device can be used to apply ultrasound to liquefy blood clots, either independently or in combination with bubbles and anti-clotting agents, possibly being used to restore blood flow to regions.

The presently disclosed device may also be focused on harnessing non-thermal properties of ultrasound therapy to generate stem cell differentiation, angiogenesis, and anti-inflammatory effects, as a treatment for a plurality of diseases including but not limited to ischemia and/or fibrosis.

In some examples, the presently disclosed device is focused on harnessing non-thermal properties of ultrasound therapy to generate anti-inflammatory effects to inhibit fibroblast proliferation.

The presently disclosed device may be focused on harnessing non-thermal properties of ultrasound therapy to generate stem cell differentiation, angiogenesis, and anti-inflammatory effects, as a treatment for a plurality of diseases including but not limited to pulmonary fibrosis, chronic obstructive pulmonary disease (COPD), respiratory syndromes and/or pulmonary embolism.

In an embodiment, the presently disclosed device is focused on harnessing thermal properties of ultrasound therapy to target and destroy tumorous cells.

In an embodiment, the presently disclosed device is focused on harnessing ultrasound therapy to target and destroy thrombus in a plurality of body regions of the user including but not limited to the lower limb region.

In an embodiment, the presently disclosed device is used to identify and/or treat deep vein thrombosis.

In some embodiments, the same transducers can be used as sensor. In some embodiments these transducers and sensors can operate in different ranges while in other embodiments, they can operate in overlapping ranges. For example, the ultrasound transducer units 114 can act as ultrasound transducer units and ultrasound sensors in some embodiments. Alternatively, the ultrasound transducers units can act as sensor units in some embodiments, and other sensor units will be used that are more aptly tuned to desired frequencies.

Machine Learning Model

A machine learning model underlying a machine learning system can be stored in a memory of device and/or the handheld computing device. The machine learning model can be trained within an adaptive clinical setting. The machine learning system can be integrated with the handheld computing device. Furthermore, the machine learning system can be executed remotely from a secondary handheld computing device. Additionally, the machine learning system can propose a recommended treatment, which can be accessed by the patient's clinician. The clinician can confirm the one or more recommended therapies including but not limited to the location, intensity, and/or frequency of the therapy.

In an embodiment, the machine learning system generates personalized ultrasound therapy for the user. For each user (patient), the machine learning system can measure the progression of the disease by comparing disease severity data in the period "A" with the disease severity data in the period "B". Based on a dataset that includes all patients and/or all patients from multiple periods, the machine learning system can train a machine learning model to correlate x-variables (patient data and ultrasound therapy specifications, etc.) with the y-variables (disease progression). Based on the trained machine learning model, ultrasound therapy specifications (while holding other x-variables such as patient characteristics constant) are adjusted to minimize predicted disease progression (or in other words, maximize the efficacy of treatment). The machine learning system may include decision tree-based machine learning models, artificial neural networks, convolutional neural networks, logistic regression, naive Bayes, nearest neighbor, support vector machines, boosted tree learning methods, and/or generative neural networks.

The presently disclosed device may be configured to receive bio-sample data of the user. In operation, the user can receive his/her bio-sample from salivary glands in a form of saliva. Then the user can place the bio-sample on a reactant material having one or more reactant properties pertaining to chemical information of the user's body. Thereafter, the user can capture an image of the reactant material upon placing the bio-sample to obtain the bio-sample data. The device can then be configured to process the bio-sample data which acts as one of the decision points for generating personalized ultrasound therapy. In an alternative embodiment, the device is configured to generate personalized ultrasound therapy based on the medicine data of the user.

The device can be configured to utilize a machine learning model underlying a machine learning system stored in the memory of the user's handheld computing device. The machine learning model can for example be trained by an adaptive clinical setting. Furthermore, the machine learning system can be integrated with the handheld computing device. Additionally, the handheld computing device can also collect information about the user's health condition through a questionnaire and/or other patient health database.

A second handheld computing device may be connected to the ultrasound therapy device, enabling remote control of the ultrasound therapy device. The machine learning system can be executed remotely from a secondary handheld computing device. Furthermore, an external computing device, such as the second handheld computing device can receive data representing ultrasonic sensor data, which is recorded as a video file.

In an embodiment the device may include a machine learning model such as a large language model (LLM), to facilitate interpretation and interaction with human language. For example, the user may record their symptoms and said LLM can interpret the description of symptoms to analyze the severity of said symptoms and/or recommend next steps for treatment, trigger an alert to a third party and/or facilitate a longer conversation with the user to elucidate the state of health of that user.

Ultrasound

Loosely organized structures, such as a thrombus or an atheroma, lacking the normal collagen and elastin fiber support, can be destroyed easily by ultrasound, but vascular walls contain a thick collagen and elastin matrix, so they tolerate ultrasound of higher intensity and lower frequency. These features are the foundation of sonothrombolysis. The present disclosure describes deploying ultrasound treatment, wherein the user receives the ultrasound therapy instructions which include disease type that needs to be treated, e.g. ischemic disease and/or organ muscle stiffness. These instructions may be predefined rules/instructions based on the user's characteristics, e.g., body size, age, type, and/or severity of organ disease—e.g., in ischemic organ disease one may want to achieve angiogenic effects that may be achieved by using ultrasound therapy parameters set at a frequency of 1/1875 MHz; 15/25 mW/cm2 spatial average temporal average (SATA); 20% duty cycle; 20 min/day).

In another example, one may want to achieve anti-inflammatory effects using parameters set at or close to a frequency of 1.5/3 MHz; 30/200 mW/cm2 SATA; 20% duty cycle; 15/20 min/day). In a further example, one may want to achieve anti-degenerative effects using parameters set at or close to a frequency of 1 MHz; 50/110 mW/cm2 SATA; 20%/50% duty cycle; 10/15 min/day). In a further example, one may want to achieve regenerative effects using parameters set at or close to a frequency of 1.5/1.6 MHz; 30/50/90 mW/cm2 SATA; 20% duty cycle; 20 min/day). In a further example, one may want to achieve differentiation effects using parameters set at or close to a frequency of 1.5/1.6 MHz; 30/50/90 mW/cm2 SATA; 20% duty cycle; 20 min/day).

The present disclosure also describes the semi-automated method of deploying ultrasound treatment. Furthermore, the present disclosure describes an automated method of deploying ultrasound treatment. For the first time usage of the automatic calibration of the wearable device to map the location and size of the user's organ, the user has to perform various steps. Additionally, for the first-time usage of manual calibration of the wearable device to map the location and size of the user's organ, the user has to perform various steps.

Positioning Mechanism

The presently disclosed device is preferably configured such that the ultrasound transducer unit and/or the physiological sensor(s) can move controllably by means of a positioning mechanism, such that the ultrasound transducer unit, e.g. with an ultrasound sensor, can move across different regions of the user's organ.

The positioning mechanism may comprise guiding channels, defining a predefined movement path, for guiding the movement of the one or more ultrasound transducer units. One advantage thereof is that the channels allow the ultrasound transducer unit to move via an automated controller that searches for the optimum signal through the movement path.

In an embodiment, the positioning mechanism can comprise a motor for engaging with the ultrasound transducer unit, and possibly a pulley engaging with the motor. In a preferred embodiment, the device can be configured such that the motor and the pulley move controllably to position the ultrasound transducer unit.

In an embodiment, the positioning mechanism comprises a micro linear actuator, which may comprise a driving side and a driven side for engaging with a motor from the driving side, and for engaging with the ultrasound transducer unit from the driven side. Additionally, the positioning mechanism may comprise a spring-based mechanism for engaging with the ultrasound transducer unit.

In an embodiment, the wearable device is configured such that the positioning mechanism provides Pulse Width Modulation (PWM) control of the ultrasound transducer unit. An average delivered power to the device can be controlled via PWM. PWM can drive the motor in on and off modes, which can be acquired by a micro-linear actuator.

Ultrasound Therapy

The device can be configured to execute a plurality of events. The wearable device can for example be configured to (utilizing the physiological sensor(s)) scan the user's organ, identify one or more regions of the user's organ, and possibly detect one or more organ diseases. The wearable device may further be configured to detect a plurality of physiological properties of a cardiovascular and tissue to optimize ultrasound therapy. Hence, the wearable device can be configured to determine an effective ultrasound therapy for the user in one or more regions of the user's organ region based on physiological properties and/or demographic characteristics. The wearable device can for example be configured to move the ultrasound transducer unit to the one or more identified regions and execute the ultrasound therapy in said one or more regions.

In an embodiment, the presently disclosed device is configured to analyze a health function of the organ of the user and to determine a location on the chest of the user where the ultrasound transducer unit is positioned based on physiological sensor data acquired minimally invasively.

As described herein, the device can be configured to create a map of the user's organ, wherein the map is stored in the memory and later be used to more efficiently position the physiological sensor(s), and/or the ultrasound transducer unit.

In an embodiment, the wearable device is configured to scan the organ by moving the ultrasound transducer unit, e.g. comprising the physiological sensor(s), across different regions of the user's organ and collect data therefrom.

In an embodiment, the wearable device is configured to compare the organ health of the user in the one or more regions to determine the efficacy of the ultrasound therapy over time. The wearable device can then be configured to update the ultrasound therapy based on the observed efficacy of the ultrasound therapy over time.

In an embodiment, the wearable device is configured to create a map of the user's organ, wherein the map is stored, e.g. in a memory of the device.

In an embodiment, the ultrasound transducer unit is configured to harness non-thermal properties of ultrasound therapy.

In an embodiment, the wearable device is configured to collect information on the user's health condition through a questionnaire and/or patient health database.

The present disclosure relates to the existing manual method of deploying ultrasound treatment. For example, the user can receive the ultrasound therapy information, comprising disease type that needs to be treated, e.g. ischemic disease and/or organ muscle stiffness. Then the user can position the ultrasound generator or the hereby disclosed device to the therapy region (therapy region can be approximated from the user's body size and demographics. E.g., if it's a small person, the user may be given a small wearable structure (e.g. a vest) to hold the wearable device in place) based on ultrasound therapy instructions. A wearable structure and/or device may include any device that can be worn by a user over longer periods of time, can be placed on a user's organ region either by the user themselves and/or able to be held in place by a user for a period of time lasting more than 10 seconds. Lastly, the user can apply (administer) the ultrasound therapy based on the instructions. These instructions may be predefined rules/instructions based on the user's characteristics, e.g., body size, age, type, and/or severity of organ disease. In a further embodiment, the user can manually adjust the pressure of the ultrasound transducer unit to the skin of the user to optimize contact with the user's skin for optimal ultrasound penetration. Said pressure adjustment can be performed using a pressure adjustment knob which moves the ultrasound transducer unit up and down. A pressure adjustment knob may in some cases be understood to be similarly constructed to a coarse adjustment knob of conventional microscopes that have been commonly used in clinical research.

The present disclosure further relates to a device configured to provide a semi-automated ultrasound treatment. Firstly, the user can receive ultrasound therapy information such as disease type that needs to be treated and therapy region, e.g. ischemic disease and/or organ muscle stiffness. The user can position the device to the therapy region using previously mapped out organ regions from the first-time use calibration process. Then the device can provide the ultrasonic data and/or electronic stethoscope data (and/or other minimally invasive physiological health data of the user) from the therapy region to the user. The user can therefore analyze the severity of the disease. The risk analysis may be assessed by a risk assessment machine learning model and/or measurement of physiological health function such as lung capacity measurement and/or a patient self-reported questionnaire, etc.). Then the user can identify the ultrasound therapy parameters such as intensity, duration, and/or pulsation frequency in one or more regions based on the user's characteristics, e.g., body size, age, type, and/or severity of organ disease (organ muscle stiffness may require an ultrasound therapy to relax the muscle and an ischemic disease may require an ultrasound therapy to get rid of plaque). Lastly, the user can administer the ultrasound therapy based on the identified therapy needs.

The present disclosure further relates to a device configured to provide an automated ultrasound treatment. The user can have access to the sensor data, such as ultrasonic data and/or electronic stethoscope data (and/or other minimally invasive physiological health data of the user) from a plurality of regions of the user. The user can therefore identify the one or more diseases and can analyze the severity of said one or more diseases in one or more regions. This can be done by employing a disease type and severity machine learning model, e.g., classification model trained on gold standards such as calcification index, plaque buildup in coronary arteries, measurement of physiological health function such as lung capacity, a patient self-reported health outcome/wellbeing questionnaire, etc. Then the user can identify the ultrasound therapy parameters (intensity, duration, and/or pulsation frequency) in one or more regions based on the user's characteristics, e.g. body size, age, type, and/or severity of organ disease (organ muscle stiffness may require an ultrasound therapy to relax the muscle and an ischemic disease may require an ultrasound therapy to shoot away plaque). Lastly, the user can administer the ultrasound therapy based on identified therapy needs.

The presently disclosed device can be configured to harness non-thermal properties of ultrasound therapy to generate stem cell differentiation, angiogenesis, and anti-inflammatory effects, as a treatment for a plurality of diseases including but not limited to ischemic organ disease and/or fibrosis. Said non-thermal properties may be achieved through increased pressure and/or amplitude to generate microstreaming (whereby increased fluid movements can promote endothelial shear stress), jetting (whereby vascular permeability can be increased), bubble expansion and/or compression (whereby vascular permeability can be increased).

Specifically, the wearable device can be configured to harness thermal effects of ultrasound through increased pulse length and/or power applied by means of the ultrasound transducer unit such that local tissue temperature, which may lead to liquefactive necrosis, can be increased.

Additionally, the wearable device can be configured to harness molecular effects. Said molecular effects may include but are not limited to the upregulation of angiogenic factors, increased nitric oxide synthase activity, anti-inflammatory properties, increased differentiation of myocytes, endothelial cells, and/or vascular smooth muscle cells.

The pulsation frequency and strength of the ultrasound transducer may be aimed at suppressing hypertrophic cardiomyopathy and/or myocardial interstitial fibrosis.

The ultrasound therapy may be aimed at enabling physiological health pacing. Alternatively, the presently disclosed device may be used to minimally invasively reduce hypertension by affecting the nerves that control blood pressure. Furthermore, low-intensity ultrasound pulsations may be used to create anti-inflammatory effects. Ultrasound pulsations may also be configured to generate anti-inflammatory effects to target systemic microvascular inflammation.

Low-intensity ultrasound pulsations may be used to enhance angiogenesis to reduce left ventricular dysfunction. Additionally, low-intensity ultrasound pulsations may be used to enhance angiogenesis to ameliorate myocardial infarction.

The presently disclosed device can be used to apply ultrasound to liquefy blood clots, either independently or in combination with bubbles and anti-clotting agents, possibly being used to restore blood flow to regions of the brain affected by stroke and/or treating arterial thrombosis and/or deep vein thrombosis.

Furthermore, the presently disclosed device may be focused on increasing myocardial blood flow in ischemic myocardium and endothelial cells. Ultrasound has direct effects on tissue that are cardioprotective which may arise from increased tissue blood flow induced by ultrasound and/or metabolites released from endothelial cells which may offer cardio protection by increasing blood flow.

The presently disclosed device may also be focused on harnessing non-thermal properties of ultrasound therapy to generate stem cell differentiation, angiogenesis, and anti-inflammatory effects, as a treatment for a plurality of diseases including but not limited to ischemic disease and/or fibrosis.

In some examples, the presently disclosed device is focused on harnessing non-thermal properties of ultrasound therapy to generate anti-inflammatory effects to inhibit fibroblast proliferation.

The presently disclosed device may be focused on harnessing non-thermal properties of ultrasound therapy to generate stem cell differentiation, angiogenesis, and anti-inflammatory effects, as a treatment for a plurality of diseases including but not limited to pulmonary fibrosis, chronic obstructive pulmonary disease (COPD), respiratory syndromes and/or pulmonary embolism.

In an embodiment, the presently disclosed device is focused on harnessing thermal properties of ultrasound therapy to target and destroy tumorous cells.

In an embodiment, the presently disclosed device is focused on harnessing ultrasound therapy to target and destroy thrombus in a plurality of body regions of the user including but not limited to the lower limb region.

In an embodiment, the presently disclosed device is used to identify and/or treat deep vein thrombosis.

Unless otherwise defined, all terms (including technical and scientific terms) used in this disclosure have the same meaning as commonly understood by one of ordinary skill in the art to which this disclosure belongs. In this specification, "mobile phone" and "smartphone" are interchangeable as are "tablet" and "smart tablet." It is to be understood that the phrases or terms employed of the present invention are for description and not of limitation. As will be appreciated by one of the skills in the art, the present disclosure may be embodied as a device, system, and method, or computer program product. Further, the present invention may take the form of a computer program product on a computer-readable storage medium having computer-usable program code embodied in the medium. The present systems and methods have been described above with reference to specific examples. However, other embodiments and examples than the above description is equally possible within the scope of the present invention. The scope of the disclosure may only be limited by the appended patent claims. Even though modifications and changes may be suggested by the persons skilled in the art, it is the intention of the inventors and applicants to embody within the patent warranted heron all the changes and modifications as reasonably and properly come within the scope of the contribution the inventors and applicants to the art. The scope of the embodiments of the present invention is ascertained with the claims to be submitted at the time of filing the complete specification. Method steps can be performed in any order unless required otherwise by the context. In the specification and claims, a feature mentioned in the singular (e.g., using "a" or "an") will be deemed to have an "at least one" or plural construction except where the context indicates such construction unworkable. A person of skill in the art will also recognize that the embodiments discussed herein are reconfigurable and within the intended scope. For example, the dependent claims from one independent claim or dependent claim can be similarly made to depend from a different independent claim and/or dependent claim, unless prohibited by the context. In addition, as would be appreciated by a person of skill in the art, certain features or elements of a claim can be mixed and matched with other features or elements, even if not presented together at the time of filing. Similarly, as would be appreciated by a person of skill in the art, data, outputs and readings from different described sensors, user inputs and other sources can be used together, even if not presented together at the time of filing. The term "and/or" in a list means all list items present, some list items present, or one of the list items present, unless such construction is limited by the context. Positional and directional terms described in this specification may be understood to be different than shown or described and should not limit the variations of embodiments possible from the claimed features that a person of ordinary skill in the art would understand from the specification, figures and claims. "Acceptable," unless the context dictates otherwise, refers to meeting a clinical threshold or such action would achieve a positive clinical outcome given the situation. "Threshold," unless the context dictates otherwise, refers to equipment or sensor operation according to best practice or achieving such a position would achieve a positive clinical outcome given the situation. "Surrounding" means around the ultrasound therapy area. "Data" as used herein can be singular or plural.

The invention claimed is:

1. An ultrasound therapy device for generating ultrasound therapy, the ultrasound therapy device comprising:
   a housing including a skin-facing side;
   a grouping of ultrasound transducer units on the skin-facing side to generate and deliver ultrasound therapy to a target therapy area of a user including at least one of a kidney region, a lung region, and a lower limb of the user, the grouping of ultrasound transducer units configured to operate directly through skin of the user near the target therapy area or indirectly through an impedance matching material, gel, or fluid near the target therapy area;
   a communications bus to receive from a minimally invasive physiological sensor a health status data of the user;
   memory including ultrasound therapy instructions; and
   a processor for processing the ultrasound therapy instructions, the ultrasound therapy instructions comprising:
      determining a non-acute health status of the user based on the health status data of the user received from the minimally invasive physiological sensor;
      receiving ultrasonic data from the ultrasound transducer units;
      determining a body location of the grouping of ultrasound transducer units from the ultrasonic data;
      transmitting ultrasound therapy information to the ultrasound transducer units;
      generating ultrasound therapy by the ultrasound transducer units and controlling with the ultrasound therapy at least one of expansion or compression of bubbles and at least one of jetting or microstreaming around the bubbles in a target therapy area of the user, after a non-acute health state of the user and the body location of the grouping has been established and determined to be acceptable; comparing health status data of pulmonary, renal, peripheral artery and/or deep vein thrombosis health of the user in one or more regions over time to determine efficacy of the ultrasound therapy; updating the ultrasound therapy based on the determined efficacy of the ultrasound therapy over time; and
      promoting one or more of angiogenesis, improve renal fibrosis and tubular injury, or neovascularization.

2. The ultrasound therapy device of claim 1, the instructions further comprise controlling by the processor at least some of the ultrasound transducer units of the grouping to be partially or fully utilized for beam steering of the ultrasound and shifting focal points of the ultrasound to a desired location of the target therapy area.

3. The ultrasound therapy device of claim 1, the processor generates an ultrasound using phased arrays of the ultrasound transducer units by adjusting a phase and a magnitude of each ultrasound transducer.

4. The ultrasound therapy device of claim 1, wherein the grouping of ultrasound transducers is arranged in an array.

5. The ultrasound therapy device of claim 1, wherein the impedance matching material comprises ultrasound gel.

6. The ultrasound therapy device of claim 1, wherein the ultrasound therapy information includes at least one of frequency, temporal average, duty cycle, and therapy duration.

7. The ultrasound therapy device of claim 1, further comprising:
   a wearable structure securable to the user,
   a positioning mechanism to position the ultrasound therapy device at a location of an optimum signal for the grouping, and
   a tightening mechanism to adjust tightness of the wearable structure around the body of the user and secure the ultrasound therapy device in position to target the target therapy area and prevent unwanted dispersion of the ultrasound,
   wherein the housing is attachable and repositionable in the wearable structure to target the target therapy area, and
   determining the body location of the grouping includes mapping a location and size of an organ of the user and determining the location of the optimum signal for the grouping.

8. The ultrasound therapy device of claim 1, wherein the ultrasound therapy instructions further comprise:
   sending and receiving ultrasonic waves from the ultrasound transducer units to test expected throughput of the impedance matching material, gel or fluid and skin contact;
   determining if expected throughput is allowable based on a pre-existing threshold; and
   instructing by the processor to start ultrasound therapy if expected throughput is allowable.

9. The ultrasound therapy device of claim 1, comprises a minimally invasive sensor for acquiring one or more of: pulmonary function information, renal function information, peripheral arterial function, deep vein thrombosis (DVT) function information of the user.

10. The ultrasound therapy device of claim 9, wherein a second acoustic sensor is facing away from the skin-facing side and the processor is configured to enable detection and removal of surrounding acoustic disturbances sensed by the second acoustic sensor that could interfere with receiving and sending signals.

11. The ultrasound therapy device of claim 1, wherein the processor carries out instructions to promote one or more of reducing inflammation and ameliorating inflammatory processes.

12. The ultrasound therapy device of claim 1, further comprising:
a circuit board in communication with at least one of the ultrasound transducer units, an acoustic sensor, a positioning mechanism, and the processor.

13. The ultrasound therapy device of claim 1, further comprises an inertial measurement unit (IMU) sensor configured to determine at least one of whether the ultrasound therapy device is correctly positioned on the skin and whether the user is moving.

14. The ultrasound therapy device of claim 1, wherein the ultrasound therapy information comprises location data, frequency data, spatial average temporal average data, duty cycle data, and therapy duration data.

15. A method of applying ultrasound therapy by a user, the method comprising steps of:
providing the user with an ultrasound therapy device containing a housing with ultrasound transducers on a skin facing side of the housing, an impedance matching material, gel or fluid, and a user interface;
applying by the user the impedance matching material, gel, or fluid at or near a target therapy area including at least one of a kidney region, a lung region, and a lower limb of the user;
holding by the user or fastening within a wearable structure the ultrasound therapy device against the impedance matching material, gel, or fluid of the user at or near the target therapy area;
sensing, by the ultrasound therapy device, and receiving, by the user interface, information regarding at least some of a location of the target therapy area, a location of the ultrasound therapy device relative to the target therapy area, an ultrasonic throughput of the impedance matching material, gel or fluid and skin contact, a type of ultrasound therapy to perform, and a health status of the user;
activating the ultrasound therapy by the user;
performing the ultrasound therapy on the user based on the information and controlling with the ultrasound therapy at least one of expansion or compression of bubbles and at least one of jetting or microstreaming around the bubbles in the target therapy area; comparing health status data of pulmonary, renal, peripheral artery and/or deep vein thrombosis health of the user in one or more regions over time to determine efficacy of the ultrasound therapy; updating the ultrasound therapy based on the determined efficacy of the ultrasound therapy over time; and
promoting one or more of angiogenesis, improve renal fibrosis and tubular injury, or neovascularization.

16. The method of claim 15, further comprising:
mapping out a sub skin layout of the target therapy area using the ultrasound transducers or other sensors on the device; and
performing the ultrasound therapy on a portion of the layout.

17. The method of claim 16, further comprising:
focusing a laser from the ultrasound therapy device or another device below the user's skin near the target therapy area to create an ultrasound emanating from a focal point of the laser.

18. An ultrasound system for generating ultrasound therapy, the ultrasound system comprising:
an ultrasound therapy device, comprising:
a housing including a skin-facing side;
a grouping of ultrasound transducer units on the skin-facing side to generate and deliver ultrasound to a target therapy area of a user including at least one of a kidney region, a lung region, and a lower limb of the user, the grouping of ultrasound transducer units configured to operate directly through skin of the user near the target therapy area or indirectly through an impedance matching material, gel or fluid near the target therapy area; and
a communications bus to receive from a minimally invasive physiological sensor a health status data of the user, and to exchange information and instructions from a processor and memory;
the memory including ultrasound therapy instructions; and
the processor for processing the ultrasound therapy instructions,
the ultrasound therapy instructions comprising:
determining a non-acute health status of the user based on the health status data of the user received from the minimally invasive physiological sensor;
receiving ultrasonic data from the ultrasound transducer units;
determining a body location of the grouping of ultrasound transducer units from the ultrasonic data;
transmitting ultrasound therapy information to the ultrasound transducer units; and
generating ultrasound therapy by the ultrasound transducer units and controlling with the ultrasound therapy at least one of expansion or compression of bubbles and at least one of jetting or microstreaming around the bubbles in a target therapy area of the user, after a non-acute health state of the user and the body location of the grouping has been established and determined to be acceptable; comparing health status data of pulmonary, renal, peripheral artery and/or deep vein thrombosis health of the user in one or more regions over time to determine efficacy of the ultrasound therapy; updating the ultrasound therapy based on the determined efficacy of the ultrasound therapy over time; and
promoting one or more of angiogenesis, improve renal fibrosis and tubular injury, or neovascularization.

19. An ultrasound therapy device for generating ultrasound therapy, the ultrasound therapy device comprising:
a housing including a skin-facing side;
a grouping of ultrasound transducer units on the skin-facing side to generate and deliver ultrasound therapy to a target therapy area of a user including at least one of a kidney region, a lung region, and a lower limb of the user, the grouping of ultrasound transducer units configured to operate directly through skin of the user near the target therapy area or indirectly through an impedance matching material, gel, or fluid near the target therapy area;
a communications bus to receive from a minimally invasive physiological sensor a health status data of the user;
memory including ultrasound therapy instructions; and
a processor for processing the ultrasound therapy instructions, the ultrasound therapy instructions comprising:
determining a non-acute health status of the user based on the health status data of the user received from the minimally invasive physiological sensor;

receiving ultrasonic data from the ultrasound transducer units;

determining a body location of the grouping of ultrasound transducer units from the ultrasonic data;

transmitting ultrasound therapy information to the ultrasound transducer units; and sending and receiving ultrasonic waves from the ultrasound transducers to test expected throughput of the impedance matching material, gel or fluid and skin contact;

determining if expected throughput is allowable based on a pre-existing threshold;

instructing by the processor to start ultrasound therapy if expected throughput is allowable; and generating ultrasound therapy by the ultrasound transducer units in a target therapy area of the user, after a non-acute health state of the user and the body location of the grouping has been established and determined to be acceptable.

20. The ultrasound therapy device of claim 1, wherein the instructions include controlling by the processor the grouping of the transducer units to localize an organ in the target therapy area;

beam steering of the ultrasound by the processor to a specific angle and a position without using any moving mechanical parts based on a region of the organ to be treated; and selectively activating ultrasound transducer units depending on the region of the organ identified as needing treatment.

21. The ultrasound therapy device of claim 20, wherein the localizing of the organ uses amplitude and time delay of the signal received by the ultrasound transducer units.

22. The ultrasound therapy device of claim 1, wherein the processor continuously monitors organ function in the target therapy area over time and adjusts the ultrasound therapy based on the organ function over time.

23. The ultrasound therapy device of claim 7, wherein the ultrasound therapy instructions include positioning, through the positioning mechanism, along a guiding channel the grouping at the location of optimum signal.

24. The ultrasound therapy device of claim 23, wherein the ultrasound therapy instructions further comprise automatically controlling by the processor the positioning mechanism to position the grouping to the location of optimum signal.

25. The ultrasound therapy device of claim 23, wherein the location of the optimum signal is searched for along the guiding channel based on output of sensors on the ultrasound therapy device and the mapping of the location and the size of the user's organ.

26. The ultrasound therapy device of claim 7, wherein the ultrasound therapy instructions include continuously updating the location of optimum signal based on output of sensors on the ultrasound therapy device, and automatically and continuously controlling the positioning mechanism to the updated location of optimum signal.

27. The ultrasound therapy device of claim 22, wherein the ultrasound therapy instructions further comprise measuring disease progression in the target therapy area over time, and updating the ultrasound therapy based on the measured disease progression over time.

* * * * *